(12) United States Patent
Roy et al.

(10) Patent No.: US 9,040,253 B2
(45) Date of Patent: May 26, 2015

(54) METHOD FOR ENHANCING RECOMBINANT PROTEIN PRODUCTION BY CELL-FREE PROTEIN EXPRESSION SYSTEM

(75) Inventors: Sushmita Mimi Roy, Sunnyvale, CA (US); Sunil Bajad, Fremont, CA (US); Evan Green, Mountain View, CA (US); Henry Heinsohn, Alameda, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 141 days.

(21) Appl. No.: 13/087,075

(22) Filed: Apr. 14, 2011

(65) Prior Publication Data

US 2011/0262946 A1    Oct. 27, 2011

Related U.S. Application Data

(60) Provisional application No. 61/324,126, filed on Apr. 14, 2010.

(51) Int. Cl.
*C12Q 1/37* (2006.01)
*G01N 33/68* (2006.01)
*C12P 21/02* (2006.01)

(52) U.S. Cl.
CPC ............ *G01N 33/6848* (2013.01); *C12P 21/02* (2013.01)

(58) Field of Classification Search
CPC ............... C12N 15/1031; A61K 2039/55516; C07K 14/005; C07K 14/195; C07K 2319/31
See application file for complete search history.

(56) References Cited

U.S. PATENT DOCUMENTS

2006/0134739 A1   6/2006   Chatterjee et al.
2008/0248521 A1   10/2008  Knapp et al.

OTHER PUBLICATIONS

Wouters et al., Proteins of *Lactococcus lactis* MG1363 are Involved in Cryoprotection and in the Production of Cold-Induced Proteins, Appl Environ Microbiol. (2001), vol. 67(11), pp. 5171-5178.*
Steinmoen et al., Induction of natural competence in *Streptococcus pneumoniae* triggers lysis and DNA release from a subfraction of the cell population., PNAS, 2002, vol. 99, pp. 7681-7686.*
Iskakova et al., Troubleshooting coupled in vitro transcription—translation system derived from *Escherichia coli* cells: synthesis of high-yield fully active proteins., Nucleic Acids Res. 2006, vol. 34(19), e135, pp. 1-9 of 9.*
RTS 100 *E. coli* HY Kit (Jan. 2006).*

(Continued)

*Primary Examiner* — Alexander Kim
(74) *Attorney, Agent, or Firm* — Kilpatrick Townsend & Stockton LLP

(57) ABSTRACT

The present invention provides a method for monitoring of profile changes of components in a dynamic system such as a cell-free in vitro protein synthesis system by using liquid chromatography (LC) combined with mass spectrometry (MS). In an additional aspect, this invention provides a method for enhancing the yield and/or reproducibility in a cell-free protein synthesis system by modulating the level and/or activity of a protein component that has regulatory effects on the system.

4 Claims, 12 Drawing Sheets

(56) References Cited

OTHER PUBLICATIONS

Cobin et al., Toward a protein profile of *Escherichia coli*: Comparison to its transcription profile., PNAS (2003), vol. 100(16), pp. 9232-9237.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Zubay, Geoffrey, In vitro synthesis of protein in microbial systems, Annu. Rev. Genet. (1973), vol. 7, pp. 267-287.*

Yamataka et al., "Induction of CspA, and *E. coli* Major Cold-Shock Protein, Upon Nutritional Upshift at 37° C.," Genes to Cells (2001) 6, 279-290.

Hofweber et al., "The Influence of Cold Shock Proteins on Transcription and Translation Studied in Cell-Free Model Systems," FEBS Journal 272 (2005) 4691-4702.

* cited by examiner

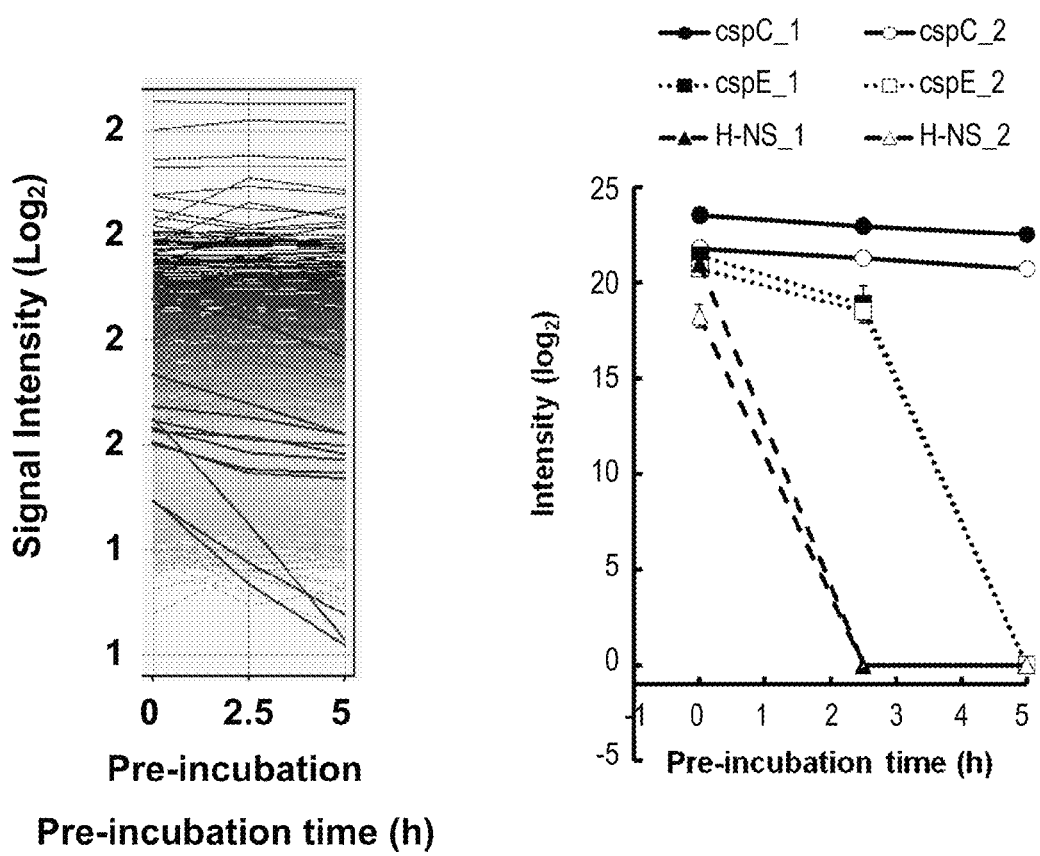
*FIG. 7C*  *FIG. 7D*

SEQUENCE LISTING

```
<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: synthetic multi-histidine affinity tag, 6x His,
      hexa-His tag, His tag

<400> SEQUENCE: 1

His His His His His His
 1               5

<210> SEQ ID NO 2
<211> LENGTH: 76
<212> TYPE: DNA
<213> ORGANISM: Artificial Sequence
<220> FEATURE:
<223> OTHER INFORMATION: synthetic PCR primer extension amplification
      primer for cold shock protein CspA

<400> SEQUENCE: 2
atatatcata tgcatcacca tcaccatcac agcggtggct ccggtaaaat gactggtatc       60
gtaaaatggt tcaacg                                                      76

<210> SEQ ID NO 3
<211> LENGTH: 41
<212> TYPE: DNA
<213> ORGANISM: Artificial Sequence
<220> FEATURE:
<223> OTHER INFORMATION: synthetic PCR primer extension amplification
      primer for cold shock protein CspA

<400> SEQUENCE: 3
atatatgtcg acttacaggc tggttacgtt accagctgcc g                          41

<210> SEQ ID NO 4
<211> LENGTH: 79
<212> TYPE: DNA
<213> ORGANISM: Artificial Sequence
<220> FEATURE:
<223> OTHER INFORMATION: synthetic PCR primer extension amplification
      primer for cold shock-like protein CspE

<400> SEQUENCE: 4
atatatcata tgcatcacca tcaccatcac agcggtggct ctaagattaa aggtaacgtt       60
aagtggttta atgagtcca                                                   79

<210> SEQ ID NO 5
<211> LENGTH: 44
<212> TYPE: DNA
<213> ORGANISM: Artificial Sequence
<220> FEATURE:
<223> OTHER INFORMATION: synthetic PCR primer extension amplification
      primer for cold shock-like protein CspE
```

```
<400> SEQUENCE: 5
atatatgtcg acttacagag cgattacgtt tgcagcagaa gggc                    44

<210> SEQ ID NO 6
<211> LENGTH: 76
<212> TYPE: DNA
<213> ORGANISM: Artificial Sequence
<220> FEATURE:
<223> OTHER INFORMATION: synthetic PCR primer extension amplification
      primer for cold shock protein DNA-binding protein H-NS

<400> SEQUENCE: 6
atatatcata tgcatcacca tcaccatcac agcggtggca gcgaagcact taaaattctg   60
aacaacatcc gtactc                                                   76

<210> SEQ ID NO 7
<211> LENGTH: 48
<212> TYPE: DNA
<213> ORGANISM: Artificial Sequence
<220> FEATURE:
<223> OTHER INFORMATION: synthetic PCR primer extension amplification
      primer for cold shock protein DNA-binding protein H-NS

<400> SEQUENCE: 7
atatatgtcg acttattgct tgatcaggaa atcgtcgagg gatttacc                48
```

METHOD FOR ENHANCING RECOMBINANT PROTEIN PRODUCTION BY CELL-FREE PROTEIN EXPRESSION SYSTEM

RELATED APPLICATIONS

This application claims priority to U.S. Provisional Patent Application No. 61/324,126, filed Apr. 14, 2010, the contents of which are hereby incorporated by reference in the entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -42-1.TXT, created on Jun. 29, 2011, 4,096 bytes, machine format IBM-PC, MS-Windows operating system, is hereby incorporated by reference in its entirety for all purposes.

BACKGROUND OF THE INVENTION

Protein synthesis is a fundamental biological process that underlies the development of polypeptide therapeutics, vaccines, diagnostics, and industrial enzymes. With the advent of recombinant DNA (rDNA) technology, it has become possible to harness the catalytic machinery of the cell to produce a desired protein. This can be achieved within the cellular environment or in vitro using lysates derived from cells.

In vitro, or cell-free, protein synthesis offers several advantages over conventional in vivo protein expression methods. Cell-free systems can direct most, if not all, of the metabolic resources of the cell towards the exclusive production of one protein. Moreover, the lack of a cell wall and membrane components in vitro is advantageous because it allows for control of the synthesis environment. For example, tRNA levels can be changed to reflect the codon usage of genes being expressed. The redox potential, pH, or ionic strength can also be altered with greater flexibility than with in vivo protein synthesis because concerns of cell growth or viability do not exist. Furthermore, direct recovery of purified, properly folded protein products can be easily achieved.

This invention relates to in vitro polypeptide synthesis in a system utilizing a suitable cell lysate. In particular, the invention provides a method for monitoring changes in the profile of various components (such as protein quantity and state of modification) within a cell-free in vitro polypeptide synthesis system, allowing the identification of components that correlate in their level or amount to the cell lysate's capacity to produce recombinant proteins in the system. The invention also provides a method for improving protein yield from the in vitro polypeptide synthesis reactions, by way of countering the changes in cell lysate components responsible for reduced protein yield, for example, by down-regulating proteins that have been identified to suppress the in vitro polypeptide synthesis and/or up-regulating proteins that have been identified to promote the in vitro polypeptide synthesis in the cell-free system. Because of the significant advantages of a cell-free in vitro polypeptide synthesis system due to its relative simplicity, there exists the need to improve the system's productivity and efficiency. The present invention fulfills this and other related needs.

BRIEF SUMMARY OF THE INVENTION

In the first aspect, this invention relates to a method for monitoring a cell-free protein synthesis system. The method comprises these steps: (a) extracting a first sample from the system at a first time point; (b) extracting a second sample from the system at a second time point; (c) digesting proteins in the first and second samples separately to produce peptides of about 6-15 amino acids in length; (d) separating the peptides according to their size and polarity; (e) determining the molecular mass and quantity of each of the peptides with greater than 10 ppm accuracy in a mass spectrometer; (f) determining the amino acid sequence and chemical composition of each peptide; and (g) comparing the quantity and chemical composition of each peptide from the first and the second samples, thereby determining the change in quantity and chemical composition of the peptides. In some embodiments, steps (a) to (f) are repeated after step (g) is completed. In other embodiments, step (c) is performed by enzymatic digestion, such as by papain, Endoproteinase Glu-C, Endoproteinase Lys-C, trypsin, or chymotrypsin digestion. In some embodiments, step (d) is performed by chromatography, such as liquid chromatography, including high performance liquid chromatography (HPLC), nano- or micro-fluidic liquid chromatography. In other embodiments, step (f) further comprises aligning the amino acid sequence of at least one of the peptides with the amino acid sequence of proteins known to be present in the system, thereby identifying the protein from which the peptide has originated. In some cases, the amino acid sequence of a multiplicity of the peptides are aligned with the amino acid sequence of proteins known to be present in the system, thereby identifying a multiplicity of proteins from which the peptides have originated. In other cases, step (g) further comprises determining the change in quantity and chemical composition of the protein or proteins. In some examples, the claimed method further comprises the step of determining the ratio of the quantity of two peptides originated from the same protein.

Using the monitoring method described above, the present inventors are able to identify proteins that impact the efficiency of the cell-free protein synthesis system. In the second aspect, therefore, this invention relates to a method for enhancing recombinant protein production in a cell-free protein synthesis system comprising a cell lysate. This method comprises the step of suppressing the level or amount of a cold shock protein in the cell-free protein synthesis system when compared with a control system where no step has been taken to regulate the cold shock protein. Suppression of the cold shock protein may be achieved by reducing the protein in total amount or in activity. In some embodiments, at least a portion of the genomic sequence encoding for the cold shock protein is deleted from the genome of the cells from which the cell lysate is made; or at least one nucleotide in the genomic sequence encoding for the cold shock protein is substituted or deleted in the genome of the cells from which the cell lysate is made; or the cold shock protein comprises a multiplicity of His residues at its N- or C-terminus, such that the protein may be readily removed from the cell lysate. To reduce the activity of the cold shock protein, a neutralizing antibody for the cold shock protein can be used, or an inhibitor of the cold shock protein or its mRNA can be used. Some exemplary cold shock proteins include CspA, CspE, H-NS, and HU-β. Furthermore, additional proteins have been shown to also negatively affect the efficiency of the cell-free protein synthesis system, such as cell division protein ftsZ (Swiss-Prot ID P0A9A6) and outer membrane protein A (ompA, Swiss-Prot ID P0A910). These proteins can be removed or suppressed in their quantity and/or activity using the same general methodologies described in this application in order to enhance the efficiency of recombinant protein production in the cell-free system.

In the third aspect, this invention relates to a method for enhancing recombinant protein production in a cell-free protein synthesis system comprising a cell lysate, and the method comprises the step of enhancing the level or activity of a protein that stabilizes or enhances energy molecules in the cell-free protein synthesis system, as compared to a control lysate where no such step is taken. This protein may be, for example, adenylate kinase, ATP synthase α, or ATP synthase β.

In the fourth aspect, this invention relates to a method for enhancing recombinant protein production in a cell-free protein synthesis system comprising a cell lysate, and the method comprises the step of increasing the level of ATP, ADP, AMP, GTP, GDP, or GMP in the cell-free protein synthesis system, as compared to a control lysate, where no such step is taken. This may be achieved by suppressing the level or activity of a protein that dephosphorylates ATP, ADP, AMP, GTP, GDP, or GMP.

DEFINITIONS

Figure 1:
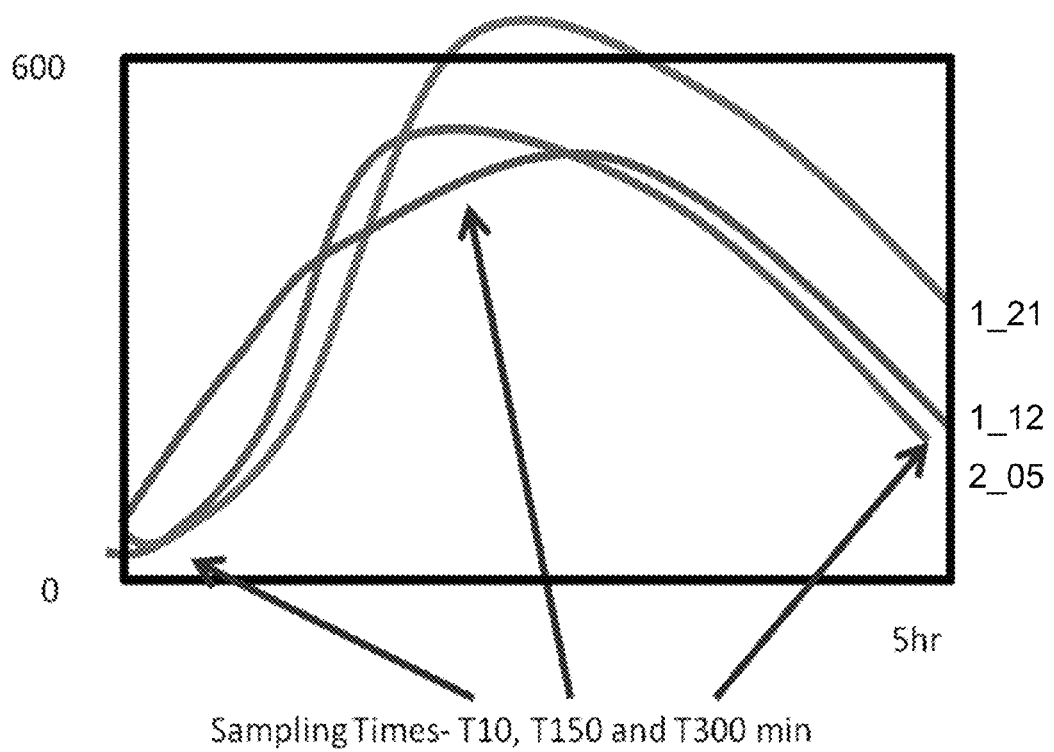
FIG. 1: $^{14}$C GMCSF profiles of three independently produced extracts used for studying pre-incubation process using proteomics and metabolomics. The arrows indicate sampling times. Extracts hit high performance at 150 minutes of incubation.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a," "and," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075. Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"In vitro synthesis" or "cell-free synthesis" refers to synthesis of polypeptides or other macromolecules in a reaction mix comprising biological extracts and/or defined reagents. The reaction mix will comprise a template for production of the macromolecule, e.g., DNA, mRNA, etc.; monomers for the macromolecule to be synthesized, e.g., amino acids, nucleotides, etc.; and co-factors, enzymes and other reagents that are necessary for the synthesis, e.g., ribosomes, uncharged tRNAs, tRNAs charged with native or non-native amino acids, polymerases, transcriptional factors, etc.

"Polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Polypeptide synthesis reaction lysate" or "synthesis reaction lysate" or "reaction lysate" or "lysate" is any cell derived preparation comprising the components required for the synthesis of polypeptides. The synthesis reaction lysate will contain protein synthesis machinery, wherein such cellular components are capable of expressing a nucleic acid encoding a desired protein where a majority of the biological components are present following lysis of the cells rather than having been reconstituted. A lysate may be further altered such that the lysate is supplemented with additional cellular components, e.g., amino acids, nucleic acids, enzymes, etc. The lysate may also be altered such that additional cellular components are removed following lysis.

An "expression cassette" is a nucleic acid construct, generated recombinantly or synthetically, with a series of specified nucleic acid elements that permit transcription of a particular polynucleotide sequence in a host cell or in a cell-free transcription/translation system. An expression cassette may be part of a plasmid, viral genome, or nucleic acid fragment. Typically, an expression cassette includes a polynucleotide to be transcribed (e.g., a polynucleotide sequence encoding a polypeptide of interest), operably linked to a promoter (e.g., a T7 promoter from the T7 bacteriophage), which means the promoter sequence is connected to the coding sequence in such a manner (e.g., typically upstream from the coding sequence) that the promoter can function to direct the proper transcription of the coding polynucleotide sequence. Optionally, the expression cassette may include additional elements such as a transcription enhancer, a polyadenylation sequence, and a selection marker (e.g., a gene encoding a protein that confers a drug-resistance to the host cell). If desired, an expression cassette may further comprise a gene encoding a reporter gene (e.g., a luciferase or a green fluorescence protein) under the transcriptional control of the promoter sequence upstream from the coding sequence.

The term "chemical composition," as used herein, encompasses all aspects of the chemical make-up of a molecule. For instance, when the "chemical composition" of a peptide is concerned, this term refers to the primary amino acid sequence as well as any chemical modification of the amino acid residues, such as the presence (or absence) of a chemical group such as —$NH_2$, —OH, —COOH, —$PO_4$, etc.

The term "profile," as used in the context of a peptide derived from a protein known to exist in a cell-free synthesis system, refers to not only the amount of the peptide, the chemical position of the peptide, but also the relative amount of the peptide to other peptides derived from the same protein.

Similarly, the "profile" of a protein encompasses the amount of the protein as well as any chemical modification occurred to the protein.

The term "modification," when used herein to describe the state of a peptide, refers to any change in chemical composition of the peptide. In other words, a peptide is deemed to have been "modified" if the primary amino acid sequence is different from that expected from a naturally occurring full length protein following enzymatic digestion, such as having at least one amino acid residue missing (shortened peptide sequence), altered in identity, at least one amino acid residue added (lengthened peptide sequence), or the presence of any additional group on any of the amino acid residues, which may be indicative of cleavage (enzymatically or otherwise) or blocked cleavage, or a chemical reaction such as oxidation/reduction, phosphorylation/dephosphorylation taken place on the protein from which the peptide has originated.

"Inhibitors," "activators," and "modulators" of a protein are used to refer to inhibitory, activating, or modulating molecules, respectively, identified using in vitro and in vivo assays for the protein's biological activity such as binding or signaling, e.g., ligands, agonists, antagonists, and their homologs and mimetics. The term "modulator" includes inhibitors and activators. Inhibitors are agents that, e.g., partially or totally block the activity of a target protein. In some cases, the inhibitor directly or indirectly binds to the target protein Inhibitors, as used herein, are synonymous with inactivators and antagonists. Activators are agents that, e.g., stimulate, increase, facilitate, enhance activation, sensitize or up regulate the activity of the target protein. Modulators include, but are not limited to, antibodies and antibody fragments, antagonists, agonists, small molecules including carbohydrate-containing molecules, siRNAs, RNA aptamers, and the like. Assays for inhibitors or activators of a target protein include, e.g., applying putative inhibitor compounds to a cell expressing the protein and then determining the functional effects on the biological activity of the protein in, e.g., binding, cellular signaling, etc. Assays for inhibitors or activators also include cell-free systems, where the samples in which the protein is exposed to a potential inhibitor are compared to control samples without the inhibitor to examine the extent of inhibition or activation. Control samples (not treated with the test compounds) are assigned a relative activity value of 100% Inhibition is achieved when the protein's activity relative to the control is about 80%, 70%, 50%, 20%, 10% or close to 0%. Similarly, activation is achieved when a test compound causes an increase in the protein's activity by at least 5%, 10%, 20%, 30%, 40%, 50%, 60%, 70%, 80%, 90% or higher such as 1- to 2-fold, 5-fold, or even 10-fold, as compared to a control.

The term "cold shock protein" encompasses all naturally occurring proteins that show an elevated level after 10 minutes at 15° C. and have 95% homology to the amino acid sequences of known cold shock proteins including cold shock-like protein CspE (SwissProt ID P0A972), DNA-binding protein H-NS (SwissProt ID P0ACF8), cold shock-like protein CspC (SwissProt ID P0A9Y6), and HU-β (SwissProt ID P0ACF4). The term "cold shock protein" encompasses all homologs, orthologs, and variants of known cold shock proteins, so long as they are specifically recognized by polyclonal antibodies generated against any one of known cold shock proteins such as those named above. Under designated immunoassay conditions, the polyclonal antibodies specifically bind to a cold shock protein at least two times the background and do not substantially bind in a significant amount to other proteins present in a test sample. For example, polyclonal antibodies raised to the CspE protein can be selected to retain only those that specifically immunoreactive with the CspE protein homologs, orthologs, or allelic variants and not with other unrelated proteins. This selection may be achieved by subtracting out antibodies that cross-react with other proteins. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically, a specific or selective reaction will provide at least twice background signal or noise, and more typically more than 10 to 100 times over background.

As used herein, "a protein that stabilizes or enhances energy molecules" is a protein that causes the increase in amount and activity of energy molecules ATP, ADP, AMP, GTP, GDP, and GMP. Examples of such proteins include adenylate kinase, ATP synthase α, and ATP synthase β. Conversely, "a protein that destabilizes or suppresses energy molecules" is a protein that causes the reduction in amount and activity of energy molecules ATP, ADP, AMP, GTP, GDP, and GMP. In particular, a protein that dephosphorylates ATP, ADP, AMP, GTP, GDP, and GMP is such a protein. Examples of such proteins include alkaline phosphatase, adenylate cyclase, and acid phosphatase.

An "inactivating antibody" or "neutralizing antibody" is an antibody or antibody fragment (e.g., an Fab fragment) that binds specifically to a particular protein (such as a cold shock protein described herein) and interferes with, reduces, or inhibits the activity of this protein as compared to the sample without the presence of such inactivating antibody. One example of such an antibody is a neutralizing anti-fibroblast growth factor (FGF) monoclonal antibody described by Shimada et al. (Clin. Cancer Res. 3897 2005; 11(10) May 15, 2005).

DETAILED DESCRIPTION OF THE INVENTION

I. Introduction

The present invention provides methods useful for monitoring the profile of components of in vitro polypeptide synthesis systems and enhancing the production yield of such systems. The methods involve the use of various means of protein analysis, such as chromatography and mass spectrometry, to monitor changes in various components (e.g., protein levels and/or modification, or concentration of a metabolite etc.) within the cell-free synthesis reaction. For example, profiles of various proteins are monitored to indicate changes in their concentration as well as chemical composition, such as changes in oxidation/reduction, amination/deamination, phosphorylation/dephosphorylation, or degradation. Also, other non-protein components of the cell-free system, such as adenosine-5'-triphosphate (ATP), nicotinamide adenine dinucleotide (NAD), nicotinamide adenine dinucleotide phosphate (NADP), and coenzyme A (CoA), and acetyl CoA can be monitored for changes in their concentration.

Such changes are then correlated with the recombinant protein production capacity of the system to identify proteins that potentially affect or regulate the productivity of the cell lysate, as well as proteins that indirectly affect the cell lysate through other components, protein or non-protein. For example, changes in ATP during the course of recombinant protein synthesis may suggest the depletion or suppressed activity of ATP-producing enzymes; decreased phosphorylation of a protein may suggest heightened activity of a phosphatase; and increased degradation of a protein may suggest the increased activity of a protease. These "regulator" proteins can subsequently be targeted to counter their negative effects on the in vitro protein synthesis system, ultimately augmenting the recombinant protein production by the system.

II. Reaction Lysate

The present invention is useful for in vitro production of polypeptides by understanding limitations of the system in the extent of activation of extract and also in the robustness of the process by which it can be made reproducibly. Modifying the extract production process will enhance the activity of the extract and make it possible to make several batches of extract reproducibly and reliably. The result is enhanced production of the polypeptide desired to be produced by the in vitro reaction.

A. Lysate Preparation

The present invention involves a recombinant protein production system based on a reaction lysate derived from a host cell for in vitro translation of a target protein. Some embodiments of the present invention are methods of monitoring in vitro polypeptide synthesis that require the generation of a reaction lysate in which the polypeptide will be recombinantly produced. Other embodiments provide the reaction lysate as a composition as described herein.

For convenience, the organism used as a source for the lysate may be referred to as the source organism or host cell. Host cells may be bacteria, yeast, mammalian or plant cells, or any other type of cell capable of protein synthesis. A reaction lysate comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, $N^{10}$-formyltetrahydrofolate, formylmethionine-tRNAf$^{Met}$ synthetase, peptidyl transferase, initiation factors such as IF-1, IF-2, and IF-3, elongation factors such as EF-Tu, EF-Ts, and EF-G, release factors such as RF-1, RF-2, and RF-3, and the like.

A bacterial lysate derived from any strain of bacteria can be used in the methods of this invention. The bacterial lysate can be obtained as follows. The bacteria of choice are grown up overnight in any of a number of growth media and under growth conditions that are well known in the art and easily optimized by a practitioner for growth of the particular bacteria. For example, a natural environment for synthesis utilizes cell lysates derived from bacterial cells grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and complex sources of nutrients. Cells that have been harvested can be lysed by suspending the cell pellet in a suitable cell suspension buffer, and disrupting the suspended cells by sonication, breaking the suspended cells in a French press, or any other method known in the art useful for efficient cell lysis. The cell lysate is then centrifuged or filtered to remove large DNA fragments.

Rabbit reticulocyte cells provide an example of a mammalian cell type that may be used to generate a lysate. Reticulocyte lysate is prepared following the injection of rabbits with phenylhydrazine, which ensures reliable and consistent reticulocyte production in each lot. The reticulocytes are purified to remove contaminating cells, which could otherwise alter the translational properties of final lysate. The cells can then be lysed by suspending the cell pellet in a suitable cell suspension buffer, and disrupting the suspended cells by sonication, breaking the suspended cells in a French press, or any other method known in the art useful for efficient cell lysis. After the reticulocytes are lysed, the lysate is treated with micrococcal nuclease and $CaCl_2$ in order to destroy endogenous mRNA and thus reduce background translation. EGTA is further added to chelate the $CaCl_2$ thereby inactivating the nuclease. Hemin may also be added to the reticulocyte lysate because it is a suppressor of an inhibitor of the initiation factor eIF2α. In the absence of hemin, protein synthesis in reticulocyte lysates ceases after a short period of incubation (Jackson, R. and Hunt, T. 1983 *Meth. In Enzymol.* 96, 50). Potassium acetate and magnesium acetate are added at a level recommended for the translation of most mRNA species. For further detail on preparing rabbit reticulocyte lysate, one skilled in the art can refer to, e.g., Sambrook et al., *Molecular Cloning: A Laboratory Manual, Second Edition* (Cold Spring Harbor Laboratory Press, Cold Spring Harbor, N.Y. 1989).

Wheat germ provides a plant cell that may be used as a host for which to generate a lysate that may be used by the methods of the present invention. Generally, wheat germ lysate is prepared by grinding wheat germ in an extraction buffer, followed by centrifugation to remove cell debris. The supernatant is then separated by chromatography from endogenous amino acids and plant pigments that are inhibitory to translation. The lysate is also treated with micrococcal nuclease to destroy endogenous mRNA, to reduce background translation to a minimum. The lysate contains the cellular components necessary for protein synthesis, such as tRNA, rRNA and initiation, elongation, and termination factors. The lysate is further optimized by the addition of an energy generating system consisting of phosphocreatine kinase and phosphocreatine, and magnesium acetate is added at a level recommended for the translation of most mRNA species. For more detail on the preparation of wheat germ lysate, see e.g., Roberts, B. E. and Paterson, B. M. (1973), *Proc. Natl. Acad. Sci. U.S.A.* Vol. 70, No. 8, pp. 2330-2334), following the modifications described by Anderson, C. W., et al., *Meth. Enzymol.* (Vol. 101, p. 635; 1983).

Lysates are also commercially available from manufacturers such as Promega Corp., Madison, Wis.; Stratagene, La Jolla, Calif.; Amersham, Arlington Heights, Ill.; and GIBCO, Grand Island, N.Y.

B. Additional Components

The in vitro protein synthesis systems in the present invention may include additional components to ensure the optimal protein production. For instance, bacterial contamination of the cell-free systems has many undesirable consequences and various antibiotics may be added to the system to suppress or eliminate bacterial proliferation. In some cases, one or more DNA gyrase inhibitors belonging to the class of quinolones or aminocoumarins can be used for this purpose. For more detailed description, see, e.g., PCT Patent Application No. PCT/US2010/020727.

III. Monitoring Component Profile in an In Vitro Polypeptide Synthesis System

In one aspect, the present invention relates to a method for monitoring the profile of components within an in vitro polypeptide synthesis system. The components being monitored may be proteins or non-protein molecules known to be present in the cell-free reaction.

A. Protein Digestion

If one or more proteins are to be monitored during the course of in vitro protein synthesis, the first step is to digest the protein(s) in order to generate small fragments of the protein(s), typically peptides of 6-15 amino acids in length. A number of proteases well known in the art and frequently used, including trypsin, papain, Endoproteinase Glu-C, Endoproteinase Lys-C, or chymotrypsin, that are suitable for the present invention. These enzymes cleave a protein at known sites and therefore generate fragments (peptides) of predictable amino acid sequence and size.

In order to monitor changes in the profiles of one or more proteins within the cell-free recombinant polypeptide synthesis system, samples from the same system are taken at different time points for analysis in an identical but parallel process. The digestion of proteins is generally carried out according to methods commonly practiced in the art.

B. Separating Peptides

Peptides in a sample can be separated using chromatography. Typically, separation is based on differences in size, charge (polarity), or hydrophobicity. With chromatography, the sample components to be separated are distributed between two phases: a stationary phase bed (column packing material) and a mobile phase that percolates through the stationary phase. The various sample components interact differently with the stationary phase, with components that interact strongly being retained for a longer periods on the column than components that do not interact or interact weakly with the stationary phase. Thus, the components can be separated and identified based on their respective elution time. Many different chromatographic methods are available, including size exclusion, ion exchange, and reverse phase, and can be used to separate peptides generated after protein digestion.

Size exclusion chromatography (SEC) separates molecules based on their size (hydrodynamic volume). When an aqueous solution is used to transport the sample through the column, the technique is known as gel filtration chromatography. Typically, the stationary phase is a porous matrix. The smaller analytes can enter the pores more easily and therefore spend more time in these pores, increasing their retention time. Conversely, larger analytes spend little if any time in the pores and are eluted quickly.

Ion exchange chromatography separates compounds according to the nature and degree of their ionic charge. The column to be used is selected according to its type and strength of charge. Anion exchange resins have a positive charge and are used to retain and separate negatively charged compounds, while cation exchange resins have a negative charge and are used to separate positively charged molecules.

Before the separation begins a buffer is pumped through the column to equilibrate the opposing charged ions. Upon injection of the sample, solute molecules (peptides, polypeptides or proteins) will exchange with the buffer ions as each competes for the binding sites on the resin. The length of retention for each solute depends upon the strength of its charge. The most weakly charged compounds will elute first, followed by those with successively stronger charges. Temperature, pH, buffer type, and buffer concentration can influence separation times.

Reverse phase chromatography is the name applied to the chromatography technique where the stationary phase is relatively more non-polar than mobile phase. Typically, the stationary phase is made up of hydrophobic alkyl chains ($-CH_2-CH_2-CH_2-CH_3$) that interact with the analyte. Three chain lengths, C4, C8, and C18, are commonly used. C4 is generally used for proteins with C8 and C18 used for peptides and polypeptides. Small molecules are continuous partitioned between the mobile phase and the hydrophobic stationary phase, while polypeptides and proteins usually are too large to partition into the hydrophobic phase and instead are adsorbed onto the hydrophobic surface. Reverse phase chromatography systems usually are run with a solvent gradient, so that as the mobile phase becomes more non-polar, a critical concentration is reached that causes desorption of the bound polypeptides and proteins. Once they are desorbed, they elute down the column. Peptides may be thought of as "sitting" on the stationary phase with most of the molecule exposed to the mobile phase and only a part of the molecule—the "hydrophobic foot" in contact with the stationary phase surface. Peptides can be separated based on subtle differences in the "hydrophobic foot" of the polypeptides being separated. These differences arise from differences in amino acid sequences and in conformation.

High performance liquid chromatography (HPLC) or high pressure liquid chromatography is a form of chromatography applying high pressure to drive the solutes through the column faster. This means that the diffusion is limited and the resolution is improved. The three chromatography techniques described above can be run as HPLC.

The peptides are typically detected as they elute from the chromatography column using their absorbance at 280 nm. The various chromatography techniques can also be coupled in-line with a mass spectrometer.

C. Monitoring Changes in Profile

1. Detecting Changes

Once the peptides in a sample are separated, they may then be analyzed using mass spectrometry (MS) to determine their profile, which includes aspects such as their molecular mass, chemical composition (amino acid sequence, the presence or absence of additional chemical groups such as phosphate group in known locations due to modification), and quantity. In some cases, a marker molecule of known quantity may be added into a sample to serve as a comparison basis to indicate the relative quantity of one or more peptides. In label-free quantification, two or more complex samples containing similar proteins in different amounts can be compared by measuring the intensity of the same molecule in two or more different samples. The same molecule is found in multiple samples by following the accurate mass-to-charge ratio, retention time and charge state of the molecule. The sample processing and LC-MS analysis should be demonstrated to not induce major changes in the intensity profiles of a control sample of similar complexity. Systematic shifts in intensity or retention time can be corrected by intensity normalization and retention time alignment, if necessary. The ratio of the intensity of a given molecule in one sample versus another then equals the relative quantities of that molecule present in the two samples being compared. Similarly, if the peptide being analyzed is modified, the relative amounts of that modification can be also be determined. In a similar fashion, non-protein components of a cell-free protein synthesis system may be analyzed and monitored by mass spectrometry, although for a small molecule (e.g., ATP) the analysis will be substantially simpler in procedure than that for a peptide.

Mass spectrometry is a technique used to identify molecules based on their mass-to-charge ratios after these molecules are ionized and accelerated in an electric field before being detected. The mass spectrometer consists of 3 components—an ion source, a mass analyzer and an ion detector. The sample to be analyzed is introduced into the ion source where it is ionized. These ions are then passed to the mass analyzer where they are separated according to their mass-to-charge ratios and then go to the ion detector and their presence is recorded and a mass spectrum is produced.

A number of different ionization methods are employed with mass spectrometry. Typically, for biochemical analyses, the ionization methods used are Electrospray Ionization (ESI) and Matrix Assisted Laser Desorption Ionization (MALDI). Electrospray ionization (ESI) and nanospray ionization, a low flow rate version of ESI, are well-suited to the analysis of polar molecules ranging from less than 100 Da to more than 1,000,000 Da in molecular mass.

During electrospray ionization, the sample is dissolved in a polar, volatile solvent and pumped through a narrow capillary. A high voltage is applied to the tip of the capillary, which is situated within the ionization source of the mass spectrometer, and as a consequence of this strong electric field, the sample emerging from the tip is dispersed as an aerosol of highly charged droplets. This process is aided by nebulizing gas flowing around the outside of the capillary that also helps to direct the aerosol towards the mass spectrometer. The charged droplets diminish in size by solvent evaporation. Eventually charged sample ions, free from solvent, are released from the droplets, some of which pass through a sampling cone into an intermediate vacuum region, and from there through a small aperture into the analyser of the mass spectrometer, which is held under high vacuum.

Matrix assisted laser desorption ionization (MALDI) works well with thermolabile, non-volatile organic compounds especially those of high molecular mass. It can be used for the analysis of proteins, peptides, glycoproteins, oligosaccharides and oligonucleotides. It is reasonably tolerant to buffers and other additives and is capable of measuring masses to within 0.01% of the molecular mass of the sample, at least up to ca. 40,000 Da. MALDI is based on the bombardment of sample molecules with a laser light to bring about sample ionization. The sample is pre-mixed with a highly absorbing matrix compound for the most consistent and reliable results, and a low concentration of sample to matrix works best. The matrix transforms the laser energy into excitation energy for the sample, which leads to sputtering of analyte and matrix ions from the surface of the mixture. In this way energy transfer is efficient and also the analyte molecules are spared excessive direct energy that may otherwise cause decomposition. Most commercially available MALDI mass spectrometers use a pulsed nitrogen laser of wavelength 337 nm. MALDI is a "soft" ionization method and so results predominantly in the generation of singly charged molecular-related ions regardless of the molecular mass, hence the spectra are relatively easy to interpret. Fragmentation of the sample ions does not usually occur.

For peptide sequence analysis, tandem mass spectrometry (MS-MS) is frequently used. In this method, typically, the mass spectrometer has two analyzers separated by a collision cell. The first analyzer is used to select user-specified sample ions arising from a particular component; usually molecular-related (i.e., $(M+H)^+$ or $(M-H)^-$) ions. These chosen ions pass into the collision cell where they are bombarded by molecules of an inert gas (e.g., argon, xenon, nitrogen) that cause fragment ions to be formed. These fragment ions are analyzed, i.e., separated according to their mass to charge ratios, by the second analyzer. With MS-MS, all the fragment ions arise directly from the precursor ions specified in the experiment, and thus produce a fingerprint pattern specific to the compound under investigation.

Peptide sequencing is possible by tandem mass spectrometry, because peptides fragment in a reasonably well-documented manner (P. Roepstorrf, J. Fohlmann, *Biomed. Mass Spectrom.*, 1984, 11, 601; R. S. Johnson, K. Biemann, *Biomed. Environ. Mass Spectrom.*, 1989, 18, 945). There are three different types of bonds that can fragment along the amino acid backbone: the NH—CH, CH—CO, and CO—NH bonds. Each bond breakage gives rise to two species, one neutral and the other one charged, and only the charged species is monitored by the mass spectrometer. The charge can stay on either of the two fragments depending on the chemistry and relative proton affinity of the two species. Hence, there are six possible fragment ions for each amino acid residue. The most common cleavage sites are at the CO—NH bonds along the amino acid backbone that provide sequence information. The extent of side-chain fragmentation detected depends on the type of analyzers used in the mass spectrometer.

Usually, peptides of approximately 2500 Da or less (i.e., less than 25 amino acids) produce the most useful data. Some peptides can generate sufficient information for a full sequence to be determined; others may generate a partial sequence of 4 or 5 amino acids, a sequence "tag" that is often sufficient to identify the protein from a database. The accuracy of the technique is sufficient to allow minor mass changes to be detected, e.g. the substitution of one amino acid for another, a post-translational modification or other chemical modification (such as glycosylation, phosphorylation, oxidation, deletion of at least one amino acid, etc.).

To ensure quality of the analysis, this step of the present invention is typically practiced at a minimal accuracy level (for example, at 10 ppm accuracy or greater) in a mass spectrometer.

2. Identifying a Source Protein

Upon determining the amino acid sequence of a peptide, it is then possible to identify the "source protein," i.e., the full length or parent protein from which the peptide has originated. This identification process can be accomplished by aligning the amino acid sequence of the peptide with a known protein sequence. A 100% match between the peptide sequence and a portion of the protein sequence would then indicate the protein as the source protein.

Methods of amino acid sequence alignment for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

3. Interpretation of Changes

The change in amount of a peptide (and therefore its corresponding protein, or the protein from which the peptide has originated) in the cell-free system can be immediately determined when the analysis as described above is completed with samples from the same system at different time points. This change in protein level, correlated with the state of production of the system, provides valuable information as to the potential effects of this protein on the system. Proteins that directly or indirectly influence the production efficiency of the system can therefore be identified.

In some cases, changes in peptide profile, such as increased modification of a certain type (oxidation, phosphorylaion, cleavage by protease), may provide indication that changes in the level and/or activity of certain enzymes present in the cell-free system are affecting the production rate of the system, which could then suggest a means to counter the undesirable effects or to enhance the desirable effects. As an example, the detection of a peptide having an amino acid sequence shorter than the expected length derived from digesting the source protein would indicate the increased activity of a protease known to cleave the source protein and generate the "clipped" fragment; whereas the detection of a peptide longer than expected may suggest the presence of a molecule bound to the source protein, therefore preventing the full digestion of the source protein. In another example, when the ratio of two peptides derived from the same source protein is seen to deviate from an expected ratio (e.g., 1 to 1), the observation may also indicate altered protease activity in the cell lysate or the presence of a molecule bound to the source protein. In short, changes observed in peptide profiles combined with knowledge of other proteins, especially enzymes, present in the system will allow one to identify the proteins relevant to the system's production efficiency and therefore devise a means to maximize the system's yield.

Changes in profile of other non-protein components of the cell-free synthesis system will similarly provide indication of relevance between certain proteins' level and activity and the system's protein production rate, therefore allowing counter measures to be taken to ensure the optimal yield of the in vitro synthesis system.

IV. Modulating the Regulator Proteins

In another aspect, the present invention provides a means to improve the production yield of an in vitro cell-free protein synthesis system by modulating one or more of these so-called regulator proteins, identified by the method described in the last section as capable of directly or indirectly influencing the system in its protein production rate. These proteins may include enzymes that produce molecules of critical importance to the protein production (e.g., ATP, CoA, acetyl CoA, NAD, NADP, phosphatidylethanolamine), enzymes that modify (e.g., oxidize/reduce, aminate/deaminate, phosphorylate/dephosphorylate, or degrade/cleave) key proteins in the system, proteins that destabilize or decrease energy molecules (such as proteins that dephosphorylate ATP, ADP, or AMP), or proteins that have a direct or indirect effect on protein yield of the system (e.g., cold shock protein CspA, CspE, DNA-binding protein HNS, cell division protein ftsZ, or outer membrane protein ompA). Depending on their particular effects on the system, these regulator proteins may be referred to as "positive regulators" (whose level and/or activity positively corresponds to the level of protein production) or "negative regulators" (whose level and/or activity negatively corresponds to the level of protein production). To maximize protein production, steps may be taken to increase the positive regulator protein(s) and/or to suppress the negative regulator protein(s).

A. Increasing a Positive Regulator Protein

Once a protein is identified as a positive regulator by the profile analysis as described above, efforts can be made to elevate the presence, in amount and/or activity, of the protein in the cell-free synthesis system. Several proteins have been recognized as proteins that stabilize or increase the level and activity of energy molecules (e.g., ATP, ADP, or AMP) and are therefore considered positive regulator proteins. Examples include adenylate kinase, ATP synthase α, and ATP synthase β. Various means for achieving this goal include, but are not limited to, introducing into the system an additional quantity of this protein from an exogenous source; enhancing the expression of the protein (e.g., introducing stronger promoters/enhancers, introducing additional copies of the gene into cell genome); and augmenting the protein's activity (e.g., by known activators or agonists).

The most straightforward method for increasing the presence of a positive regulator in a cell-free system is to simply add more of the protein into the system. The additional protein may be isolated from a naturally occurring source or may be recombinantly produced from another expression system.

In the alternative, a higher level of the positive regulator protein may be achieved by promoting the protein's expression in cultured cells before lysates are made from them or co-expressing them in the cell-free system. Known compounds capable of specifically boosting the gene expression may be used for this purpose. Otherwise, genetic modifications can be made to produce cells containing an elevated level of this protein and the cells then used to produce lysate for in vitro protein synthesis. One possible modification to cell genome is introducing a promoter and/or enhancer that leads to increased transcription and ultimately increased expression of the positive regulator protein. The stronger promoter/enhancer may either replace the endogenous promoter/enhancer, or may be introduced to act in addition to the endogenous counterpart. Another possibility is to introduce additional copy or copies of the gene encoding the positive regulator protein, such that additional quantity of the protein will be produced by the cells. Methods for genetic manipulation of cellular genome and creating genetically modified cell lines are well known in the art and also discussed in the sections below.

A further possibility of suppressing the effect of a positive regulator protein on a cell-free protein synthesis system is by adding known activators or agonists of the protein into the cell lysate.

B. Suppressing a Negative Regulator Protein

Similarly, after a protein is identified as a negative regulator by the profile analysis as described herein, efforts can be made to eliminate or suppress the presence, in amount and/or activity, of this protein in the cell-free synthesis system. Proteins that destabilize or suppress the level or activity of energy molecules, for example, proteins that dephosphorylate ATP, ADP, or AMP, are such negative regulator proteins. Various means for achieving this goal include, but are not limited to, interference with the expression of the protein (e.g., by disrupting its genomic sequence or transcription/translation mechanism) and inhibition of the protein's activity (e.g., by known inhibitors or antagonists such as neutralizing antibodies).

1. Inhibitory Nucleic Acids

Inhibiting the expression of a negative regulator protein (e.g., a cold shock protein) in the cells that are used later for making cell lysates for the in vitro protein synthesis system can be achieved through the use of inhibitory nucleic acids. Inhibitory nucleic acids can be single-stranded nucleic acids or oligonucleotides that can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

In one embodiment, the inhibitory nucleic acid can specifically bind to a target polynucleotide. Administration of such inhibitory nucleic acids can minimize the negative effect of a cold shock protein on a cell-free protein synthesis system by reducing or eliminating the expression of the cold shock protein. Nucleotide sequences encoding the cold shock proteins are known for several species, including cold shock-like protein CspE (SwissProt ID P0A972), DNA-binding protein H-NS (SwissProt ID P0ACF8), cold shock-like protein CspC (SwissProt ID P0A9Y6), Adenylate kinase (SwissProt ID P69441), HU-β (SwissProt ID P0ACF4), and ATP synthase. Other regulator proteins such as cell division protein ftsZ (Swiss-Prot ID P0A9A6) and outer membrane protein A (ompA, Swiss-Prot ID P0A910) are also known in their protein and encoding polynucleotide sequences. One can derive a suitable inhibitory nucleic acid from these particular cold shock proteins, their species homologs, and variants of these sequences.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation Inhibitory nucleic acid methods therefore encompass a number of different approaches to altering expression of specific genes that operate by different mechanisms. These different types of inhibitory nucleic acid technology are described in Helene and Toulme (1990) *Biochim. Biophys. Acta.*, 1049:99-125.

Inhibitory nucleic acid approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme, supra.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress translation of mRNA encoding critical proteins. For example, an inhibitory antisense nucleic acid complementary to regions of a target mRNA inhibits protein expression (see, e.g., Wickstrom et al. (1988) *Proc. Nat'l. Acad. Sci. USA* 85:1028-1032 and Harel-Bellan et al. (1988) *Exp. Med.*, 168:2309-2318). As described in Helene and Toulme, supra, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme, supra.

The inhibitory nucleic acids can also be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids can be effected by attaching to the inhibitory nucleic acid a substituent that can be activated to induce cleavage reactions. The substituent can be one that effects either chemical, photochemical or enzymatic cleavage. For example, one can contact an mRNA:antisense oligonucleotide hybrid with a nuclease which digests mRNA:DNA hybrids. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

Inhibitory nucleic acids can also include RNA aptamers, which are short, synthetic oligonucleotide sequences that bind to proteins (see, e.g., Li et al. (2006) *Nuc. Acids Res.* 34: 6416-24). They are notable for both high affinity and specificity for the targeted molecule, and have the additional advantage of being smaller than antibodies (usually less than 6 kD). RNA aptamers with a desired specificity are generally selected from a combinatorial library, and can be modified to reduce vulnerability to ribonucleases, using methods known in the art.

2. Inactivating antibodies

Inhibition of the activity of a negative regulator protein such as a cold shock protein can be achieved with an inactivating antibody or neutralizing antibody. An inactivating antibody can comprise an antibody or antibody fragment that specifically binds to the target protein, thereby interfering with the normal activity of the protein. Inactivating antibody fragments include, e.g., Fab fragments, heavy or light chain variable regions, single complementary determining regions (CDRs), or combinations of CRDs with target protein-binding activity.

Any type of inactivating antibody may be used according to the methods of the invention. The antibody can be derived from any appropriate organism, e.g., mouse, rat, rabbit, gibbon, goat, horse, sheep, etc.; or it can be a chimeric antibody derived from two different species. The inactivating antibodies, which can be polyclonal or monoclonal antibodies, are added into a cell-free system to counter the undesirable effects of a negative regulator protein. Polyclonal and monoclonal antibodies can be generated by any method known in the art.

3. Modification of a Genomic Sequence

Inhibition of a negative regulator protein can also be achieved by genetically modifying the genomic sequence encoding this protein in the cells that are to be used for producing the cell lysate, such that the protein expression is abolished or reduced in amount, or the expressed protein has no or diminished activity. Possible modifications include, but are not limited to, deletions (partial or complete), substitutions (e.g., point mutations), or insertions within the open reading frame (ORF) of the gene, as well as similar manipulations within the non-coding region, such as the upstream region from ORF, where elements responsible for transcription (e.g., promotor and enhancer) are located.

A variety of mutation-generating protocols are in the art, and can be readily used to modify a polynucleotide sequence encoding a regulator protein for the cell-free system. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Methods for producing genetically modified cell lines are described and frequently practiced in the art. For instance, retroviral vectors or other integration vectors can be used to introduce a polynucleotide sequence into a hose cell genome so that the target genomic region is modified, e.g., replaced, deleted, or otherwise disrupted. The design of retroviral vectors and other integration vectors is well known to those of ordinary skill in the art. Preparation of retroviral vectors and their uses are described in many publications including, e.g., European Patent Application EPA 0 178 220; U.S. Pat. No. 4,405,712; Gilboa, *Biotechniques* 4:504-512 (1986); Mann et al., *Cell* 33:153-159 (1983); Cone and Mulligan, *Proc. Natl. Acad. Sci. USA* 81:6349-6353 (1984); Eglitis et al., *Biotechniques* 6:608-614 (1988); Miller et al., *Biotechniques* 7:981-990 (1989); and WO 92/07943.

In some cases, the genetically modified cells will harbor a selection marker introduced during the modification process, such that the modified cells can be readily selected from their parent, unmodified cells.

4. Removal of Negative Regulator Proteins

As a further alternative, negative regulator proteins can be physically removed from the cell lysate to eliminate their inhibitory effect on protein synthesis. For example, a negative regulator protein may be removed from a cell lysate by passing the lysate through a column on which an antibody that specifically binds the negative regulator protein has been immobilized.

As another example, cells to be used for making lysate may be genetically modified using methods mentioned in the previous sections such that the genomic sequence encoding the negative regulator protein now includes a "tag" or a partner in an affinity-based binding pair, which permits quick and easy removal of the negative regulator protein from the system. The tags are typically placed at the protein's N- or C-terminus.

A frequently used affinity tag is a multi-histidine tag (e.g., 6x His; SEQ ID NO:1), which has an affinity towards nickel or cobalt ions. If one immobilizes nickel or cobalt ions on a solid carrier, such as a resin column, the His-tagged negative regulator proteins can be easily depleted from a cell lysate by running the lysate through the column. Such techniques are well known in the art, and His-tag vectors are commercially available from manufacturers such as Qiagen (Valencia, Calif.), Roche Applied Science (Rotkreuz, Switzerland), Bio-sciences Clontech (Palo Alto, Calif.), Promega (San Luis Obispo, Calif.), and Thermo Scientific (Rockford, Ill.).

Similar to the His tag, other affinity tags can be fused to a negative regulator protein, which allows rapid removal of the protein by immunoaffinity based separation technique such as immunoaffinity chromatography. Exemplary tags may include, but are not limited to, Green Fluorescent Protein (GFP) tag, Glutathione-S-transferase (GST) tag, and the FLAG-tag tag. Immunoaffinity chromatography methods are well known in the art. For more detail on either affinity or immunoaffinity chromatography, see, e.g., *Affinity Chromatography: Principles & Methods* (Pharmacia LKB Biotechnology 1988); and Doonan, *Protein Purification Protocols* (The Humana Press 1996).

EXAMPLES

The following examples are provided by way of illustration only and not by way of limitation. Those of skill in the art will readily recognize a variety of non-critical parameters that could be changed or modified to yield essentially the same or similar results.

Example 1

Sampling and Analysis of Pre-incubation Time Points

FIG. 1 shows the protein yields for rhGM-CSF (Granulocyte macrophage colony stimulating factor) obtained during a 5 hr cell-free synthesis reaction from extracts prepared as a function of different pre-incubation times for 3 different extracts. An optimal pre-incubation time of ca. 2.5 hours is required to fully activate the extract. Without pre-incubation the extract is inactive (at time 0).

High throughput proteomic profiling of individual preincubation time point samples was carried out as follows. A 96-well plate sample preparation method was developed for reducing, alkylating, proteolysing and desalting the various time point samples. Digested peptides were separated and analyzed on an HPLC system interfaced to an electrospray ionization quadrupole-time of flight (ESI-QTOF 6520 from Agilent Technologies, Santa Clara, Calif.) mass spectrometer. Sixty LC-MS/MS experiments were conducted to identify ~2000 proteins in these extracts. Software from Agilent Technologies was beta-tested for label-free differential quantification of identified proteins. Global changes in oxidation, deamidation, and proteolysis were monitored. The effects of upstream processing variables on extract performance were then correlated with the composition and dynamics of the proteome.

Example 2

LC-MS Analysis of Extract Proteome to Identify Changing Protein Levels

Five microliters of bacterial extract was sufficient to profile ~2000 proteins by 1DLC-MS without need for 2D separation. Label-free differential profiling based quantification was validated with spiked proteins. Related co-efficients of variation for sample processing and LC-MS were within 15% for majority of measurements. No retention time correction or intensity normalization was required due to high retention time and signal stability over multiple runs. Overall, a state-of-the-art sample preparation as well as LC-MS and LC-MS/MS based relative quantification platform was developed and validated for profiling ~2000 proteins in crude bacterial lysates using commercially available hardware and software. Initially, about 400 proteins were profiled in the extracts. The majority of the proteins such as elongation factor Tu, elongation factor G, elongation factor Ts, pyruvate dehydrogenase, tRNA synthetases, chaperonins, 50s and 30s ribosomal proteins don't change in concentration. Comparison of several extracts including extract 3_13 and production runs 1, 2, 4 and 5 suggest that the translation machinery related proteins such as ribosomal proteins, elongation factors and initiation factors are at comparable levels in these samples.

Figure 2:
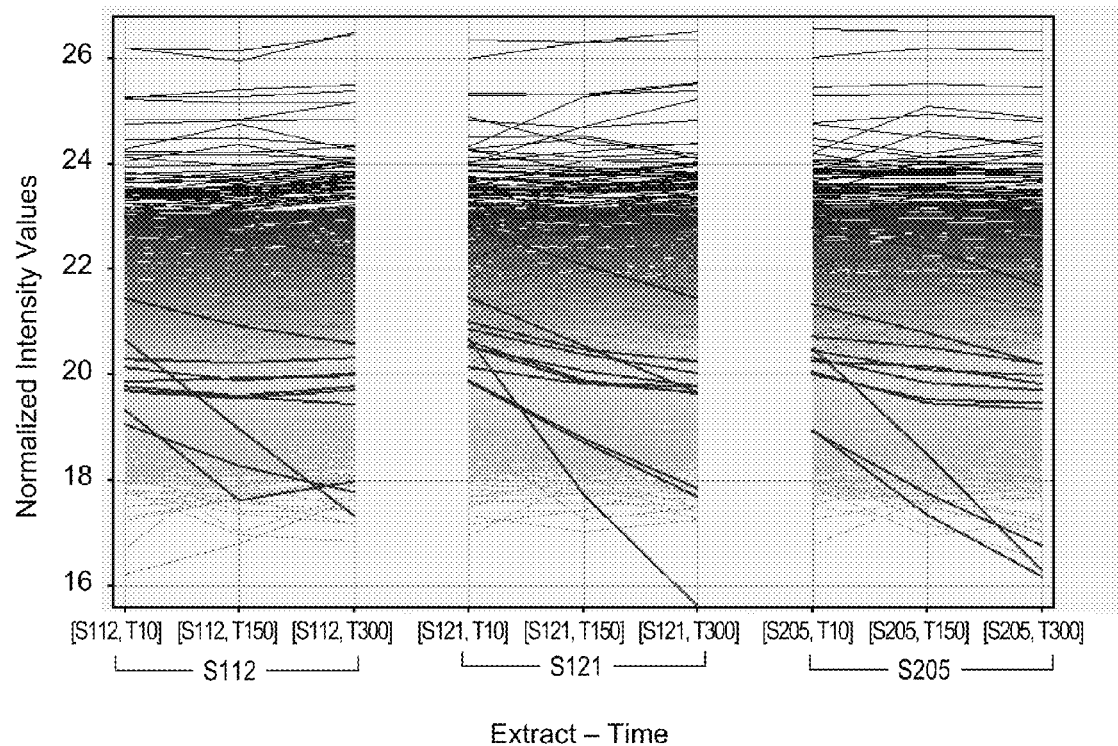
FIG. 2: High throughput proteomic profiling shows that proteins HNS, CspE, Adenylate kinase, and ATP synthase declined over pre-incubation in three different extracts. Many other proteins profiled remained the same.

Only few proteins were observed to change dramatically during pre-incubation in a background of several hundred proteins that did not change significantly in levels (FIG. 2). During the pre-incubation step before cell-free transcription and translation, the levels of these proteins decreased and corresponded to the activation of translation.

The most dramatic change in levels was observed in 3 proteins from the cold shock family. These were CspC, CspE and DNA binding HNS protein. An additional cold shock related protein HU was also found to decrease.

Cold shock proteins are known to be involved in the adaptation of cells at lower temperatures. These proteins bind to DNA/ribosomes and inhibit transcription/translation (Gualerzi et al., *J. Mol. Biol* (2003) 331, 527-539). Several experiments were conducted to understand if these changes were just an unrelated consequence of pre-incubation or whether these cold shock proteins were playing a significant role in extract activation by pre-incubation. The analysis of these proteins was pursued to understand if these cold shock proteins were being produced in cells during fermentation or whether they were induced by the processing of extracts done at cold temperatures.

Example 3

Addition of Cold Shock Proteins Inhibits Cell-Free Protein Synthesis

Figure 3:
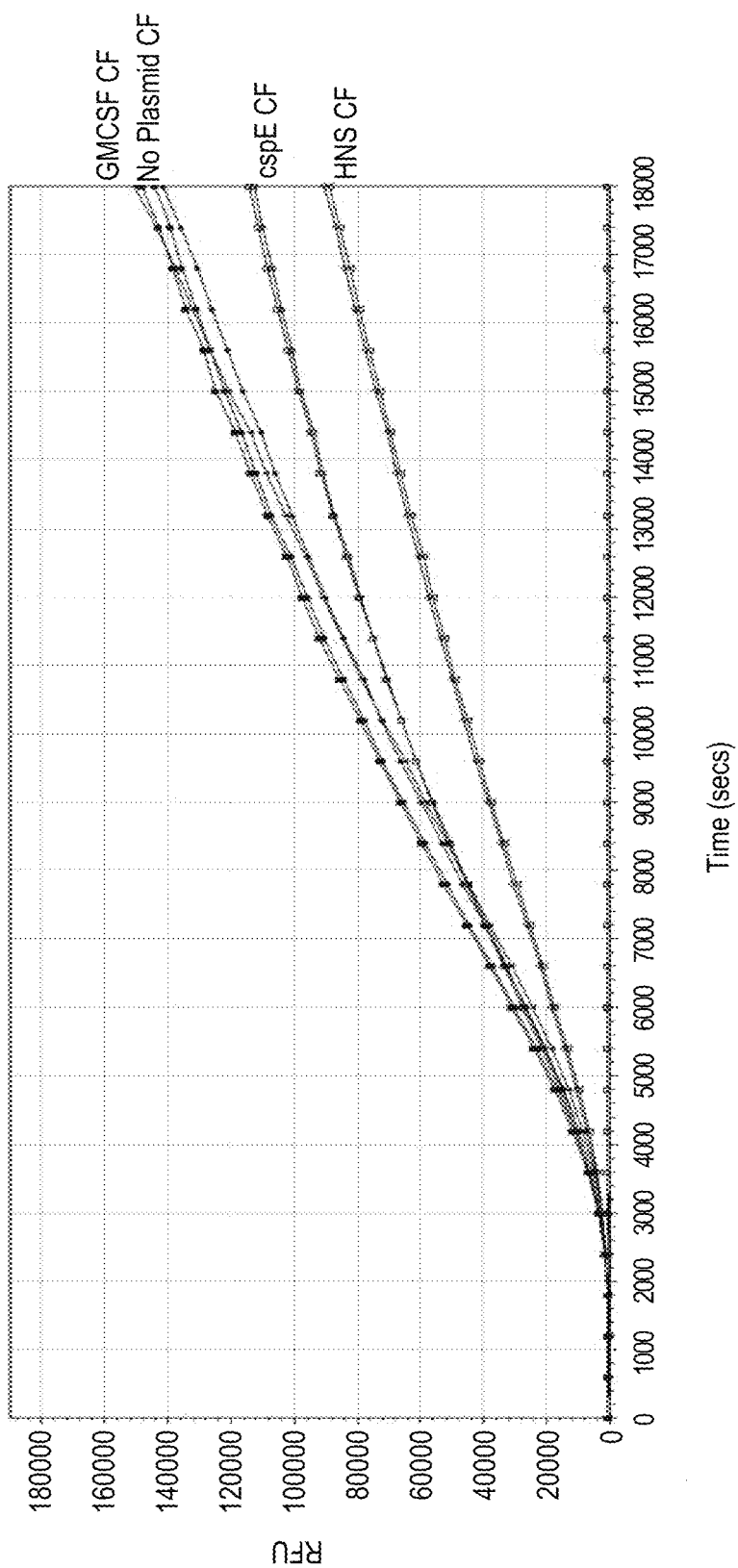
FIG. 3: Plots of GFP production in a cell-free reaction with and without cold-shock proteins CspE and H-NS. Addition of a crude lysate from a cell-free reaction with no plasmid or with a GM-CSF plasmid shows expression of GFP at high levels. Adding crude lysate preparations of cold shock proteins CspE and H-NS show a marked decrease in GFP production, indicating the inhibitory effect of cold shock proteins HNS and CspE.
Figure 4:
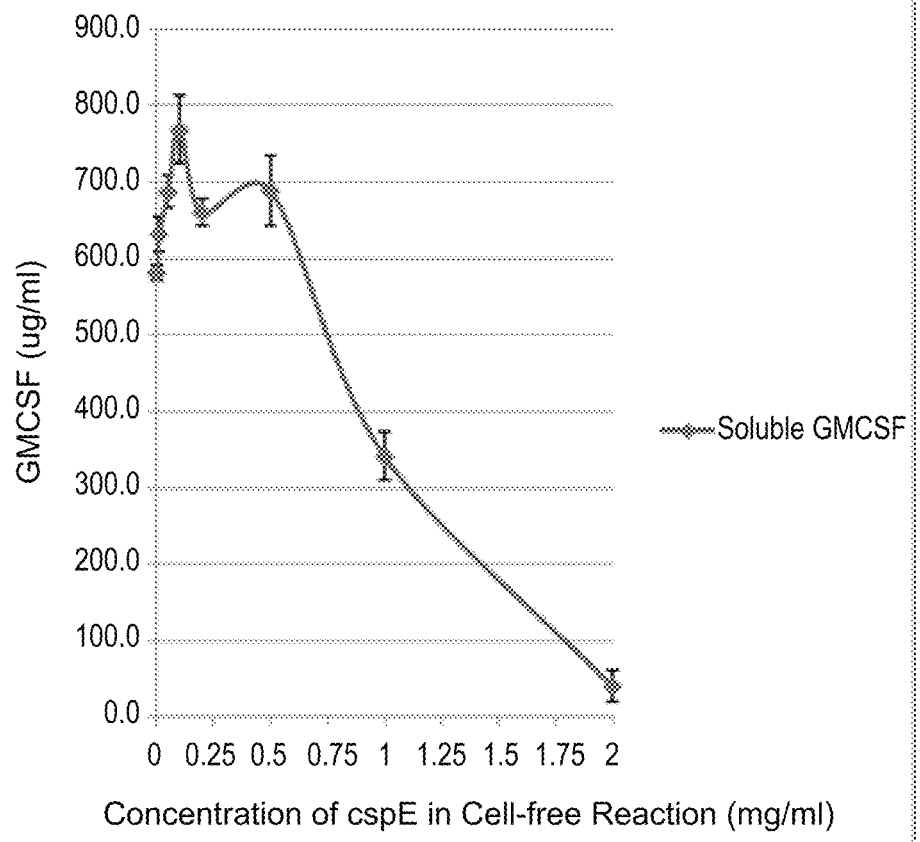
FIG. 4: Addition of CspE protein to the cell-free reaction inhibits cell-free synthesis. This indicates that CspE is a major inhibitory protein in the in vitro system and explains why warming of the extract during pre-incubation results in decrease of CspE leads to extract activation.

Cold shock proteins CspE and HNS were cloned and overexpressed in the cell-free system. Crude preparations of CspE and H-NS synthesized using cell-free reaction were added to a cell-free reaction to produce green fluorescent protein (GFP). A negative control was done using crude preparation of GM-CSF synthesized during cell-free reaction and added to a GFP cell-free reaction. The negative controls showed that the crude lysate background did not have any inhibitory effect with the no plasmid and the GMCSF lysates. However, the added crude lysates with expressed cold shock proteins were found to inhibit the cell-free reaction (FIG. 3). In the crude lysates experiment the maximum amount of HNS and CspE present was limited by their expression level, thus full inhibition was not observed. To see full inhibition these proteins were expressed in larger scale and purified. The pure protein was checked by LC-MS for correct intact mass. Addition of pure CspE to the cell-free reaction inhibits cell-free synthesis (FIG. 4).

Example 4

Introduction

*E. coli* cell-free protein synthesis (CFPS), which uses extract prepared from cells, can direct most, if not all, of the metabolic resources of the cell towards the exclusive production of the desired protein. However, the prepared extracts are inactive and require a pre-incubation step to activate transcription/translation processes, commonly referred to as the translation "run-off reaction" or "pre-incubation." It is believed that this activation process involves freeing of ribosomes bound to endogenous mRNAs. Contrary to this belief, in this disclosure the present inventors show that the inactive extract contains free ribosomes as evidenced by the synthesis of polyphenylalanine, and that pre-incubation is required even after removal of endogenous mRNAs. In the absence of hypotheses, using global label-free proteomic profiling of the extract, the inventors have discovered that activation results from the removal of cold shock proteins (CSPs) CspE, CspC, CspA, and H-NS, well known inhibitors of protein synthesis. Involvement of CSPs in the process was confirmed by the observation that pure protein preparations inhibit in-vitro protein synthesis and their deletion from the parent strain results in faster activation and higher protein synthesis activity. It is further shown that the cell harvesting and extract preparation process, typically performed at temperatures below 15° C., evokes a cold shock response and that the rapid chilling of cells leads to a robust high-yield protein production. In summary, experimental data presented herein provides new insight into the cell-free extract pre-incubation process which involves removal of the family of transcription/translation inhibitory factors, the cold shock proteins. This is the first known instance where in-depth unbiased proteomic profiling by LC-MS is successfully used to help develop a robust, commercial-scale bioprocess.

Cell-free protein synthesis is a commonly used biochemical tool in biological research and played a significant role in deciphering the genetic code (Nirenberg 2004 *Trends Biochem Sci* 29:46-54). More recently, it has become a powerful alternative to cell-based techniques for laboratory scale to commercial scale synthesis of not only small proteins but functional antibodies (Jermutus et al., 1998 *Curr Opin Biotechnol* 9: 534-48; Kanter et al., 2007 *Blood* 109: 3393-9). In-vitro protein synthesis platform offers several advantages over conventional methods, including expression of toxic proteins (Orth et al., 2011 *Toxicon* 57: 199-207), incorporation of non-natural amino acids (Noren et al., 1989 *Science* 244: 182-8; Kodama et al., 2010 *J Biochem* 148: 179-87), use of PCR fragment or mRNA as a template and high-throughput screening of gene products (Sawasaki et al., 2002 *FEBS Lett* 514: 102-5). Since the description of an in-vitro system in the early 1960s (Nirenberg 1963. *Methods Enzymol* 6: 17-23), there have been several attempts to understand the factors that influence the performance of the system (Calhoun and Swartz 2005 *Biotechnol Prog* 21: 1146-53; Jackson et al., 1983 *FEBS Lett* 163: 221-4). However, most of the effort has been devoted to improving the protein yield by optimizing message or supply of reagents or extending the applications of this technique. There has been no systematic effort on mechanistic understanding of the requisite pre-incubation process, commonly referred to as "the run-off reaction" (Nirenbuerg 2004 supra; Liu et al., 2005. *Biotechnol Prog* 21: 460-5). This process takes 80-160 min to complete, depending on the temperature, and is presumed to be required for the removal of endogenous message from polysomes. However, this presumption seems untenable considering that the inactive extract contains mostly free 70S ribosomes and subunits with relatively small amount of polysomes (Liu et al., supra; Chliamovitch and Anderson 1972. *FEBS Lett* 23: 83-6). The current hypothesis is that the process possibly involves removal of certain inhibitory factors, or activation of factors required for transcription/translation. (Liu et al., supra). In this study, the inventors applied label-free differential proteomic profiling to investigate the role of protein factors in the activation process. Their study shows that the CSPs are a significant inhibitory factor and their removal leads to activation.

Methods

Cell-Free Extract Preparation—

Cell-free extracts were generated from high cell density cultures of *E. coli* strain KGK10, as described by Zawada et al., supra. Briefly, rapidly growing cells were harvested at mid-log phase by cooling recirculation through a heat exchanger for over an hour until the temperature reached below 10° C. The cells were then pelleted in a pre-cooled (4° C.) centrifuge and washed with ice cold S30 buffer, followed by homogenization and clarification by centrifugation to yield an inactive cell-free extract. A modified "run-off procedure" (Liu et al., supra; Schindler et al., 2000 *Electrophoresis* 21: 2606-9) was used to activate the cell-free extract. To investigate the role of endogenous message in run-off reactions, extract was incubated with 150 U/ml of *Staphylococcus aureus* nuclease (EMD chemicals, Gibbstown, N.J., USA) and 1 mM calcium chloride for up to 60 min at 30° C. (Pelham and Jackson 1976. *Eur J Biochem* 67: 247-56).

Cell-Free Protein Synthesis—

The inventors used cell-free expression of rhGM-CSF, a 15 kD 4-helix bundle human cytokine, to monitor the protein synthesis activity of the extract (Zawada et al., supra). Reactions were run at 30° C. containing 8 mM magnesium glutamate, 10 mM ammonium glutamate, 130 mM potassium glutamate, 35 mM sodium pyruvate, 1.2 mM AMP, 0.86 mM each of GMP, UMP, & CMP, 2 mM amino acids (1 mM for tyrosine), 4 mM sodium oxalate, 1 mM putrescine, 1.5 mM spermidine, 15 mM potassium phosphate, 100 nM T7 RNA polymerase, 2-50 nM DNA template(s), 1-10 μM E. coli DsbC, and 33% (v/v) IAM-treated cell-free extract (Zawada et al., supra). Yields of soluble rhGM-CSF were monitored by 14C leucine incorporation as described by Zawada et al., supra.

For polyphenylalanine synthesis, 0.4 mg/ml of polyuridylic acid (Sigma, St. Louis, USA) was used as a template instead of plasmid. For studying the effect of cold shock proteins on in-vitro translation, highly purified cold shock proteins were added at the beginning of the cell-free reaction at the indicated concentrations.

Label-Free Differential Proteomic Profiling—

Extract samples collected during the pre-incubation process were centrifuged and denatured with 6 M guanidine hydrochloride followed by reduction (10 mM DTT) and alkylation (25 mM iodoacetic acid). Digestion was performed with modified porcine trypsin (Promega, Madison, USA) by overnight incubation at 37° C. Desalting was performed on Sep-Pak tC 18 96 well solid phase extraction plate (Waters, Milford, USA). Samples were analyzed by liquid chromatography (Agilent 1200 Rapid Resolution) coupled to qTOF mass spectrometer (Agilent 6520). Peptides were separated on reverse phase column (Zorbax SB C18, 50×3 mm) with 0.1% formic acid in water (solvent A) and 0.1% formic acid in acetonitrile (solvent B) at flow rate of 0.5 ml/min. Gradient was as follows: 0-2 min—2% B, 40 min—45% B, 40.01 min—90% B, 45 min—90% B, 45.01-55 min—2% B. The mass spectrometer was operated in positive ionization mode with ESI voltage 4000 V, source temperature 325° C., nebulizer gas 35 psi and fragmentor voltage 160 V. For generating peptide library, the mass spectrometer was operated in MS/MS mode with the 6 most intense precursor ions selected for fragmentation. A total of 64 MS/MS runs with split mass ranges were performed with the peptides identified in the previous MS/MS run/s excluded from the analysis in the subsequent MS/MS runs. Peptide MS/MS data was searched against E. coli K12 database (UnprotKB/Swiss-Prot) using Spectrum Mill® software version A.03.03 (Agilent, Santa Clara, USA). For creating an in-house peptide database containing chemical formula, mass and RT, identified peptides were assigned a chemical formula by using Software tool Molecular Weight Calculator V6.46 (web site: omics.pnl.gov/software/MWCalculator.php).

For profiling studies, the mass spectrometer was operated in MS mode with scanning range of 300-1700 amu and data was searched against the described in-house peptide library for peak finding, extraction and integration using MassHunter® software Version B.03.01 (Agilent, Santa Clara, Calif.). The processed data was further analyzed and visualized by Mass Profiler Professional® version 2.0 (Agilent, Santa Clara, Calif., USA).

Deletion of Cold Shock Proteins—

The ΔcspE, ΔcspE+ΔcspA, ΔcspE+ΔcspA+ΔcspC, and ΔcspE+ΔcspA+Δhns mutant strains were constructed by P1 phage transduction of the gene deletion mutants from the Keio collection of E. coli K-12 mutants with in-frame, single-gene knock-outs (16) obtained from The Coli Genetic Stock Centre (CGSC) at Yale University. The single-gene mutant strains ΔcspA, ΔcspC, ΔcspE and Δhns are CGSC#10603, 9515, 11860 and 9111, the respective genes of which were replaced by kanamycin resistant genes. P1 phage lysate from these single-gene knock-out mutants was transduced into the target strains in this study. Kanamycin resistant recombinant strains were isolated and gene deletion in the mutant strain was confirmed by colony PCR using a pair of primers which are designed according to the sequences upstream and downstream of the deleted gene. Then kanamycin resistant gene was eliminated by using a FLP recombinase encoding plasmid, 706-FLP (Gene Bridges, Heidelberg, Germany). After elimination of the antibiotic resistant gene, the next gene deletion can be introduced into the mutant strain and selected by the same method.

Cold Shock Protein Expression and Purification—

The genes encoding CspA, CspE and H-NS were amplified using E. coli strain A19 genomic DNA as templates. A hexa-His (SEQ ID NO:1) tag encoding sequence and a SGG short linker encoding sequence were ligated to the 5'-end of the cold shock protein genes by PCR primer extension. The primer sequences used to amplify the cold shock protein genes include 5'-ATATATCATATGCATCACCATCACCAT-CACAGCGGTGGCTCCGGTAAAATGACTGGT ATCG-TAAAATGGTTCAACG-3' (SEQ ID NO:2) and 5'-ATATAT-GTCGACTTACAGGCTGGTTACGTTACCAGCTGCCG-3' (SEQ ID NO:3) for CspA 5'-ATATATCATATGCATCACCATCACCAT-CACAGCGGTGGCTCTAAGATTAAAGGTAAC GTTAAGTGGTTTAATGAGTCCA-3' (SEQ ID NO:4) and 5'-ATATATGTCGACTTACAGAGCGAT-TACGTTTGCAGCAGAAGGGC-3' (SEQ ID NO:5) for CspE, 5'-ATATATCATATGCATCACCATCACCAT-CACAGCGGTGGCAGCGAAGCACTTAAAATT CTGAACAACATCCGTACTC-3' (SEQ ID NO:6) and 5'-ATATATGTCGACTTATTGCTTGATCAG-GAAATCGTCGAGGGATTTACC-3' (SEQ ID NO:7) for H-NS. After PCR amplification, the DNA was purified using QIAGEN PCR purification spin column and digested by restriction enzymes, NdeI and SalI. The restriction digested DNA was ligated into our expression vector pYD317, which is a high-copy number plasmid with a T7 RNA polymerase controlled expression cassette. The cspC gene was synthesized (DNA 2.0, Menlo Park, Calif., USA) and subcloned into pYD317.

CSPs were expressed using cell-free reactions (100 ml) and purified by FPLC (Akta Explorer 100) by IMAC (Ni Sepharose 6 FF, GE Healthcare Bio-Sciences Corp, Piscataway, USA) with a linear gradient of 20 mM imidazole to 350 mM imidazole in 50 mM Tris-HCl buffer (pH 7.9) containing 350 mM NaCl. The pooled fractions containing protein were further purified by anion exchange chromatography (Q Sepharose FF, GE Healthcare Bio-Sciences Corp, Piscataway, USA) using a linear gradient of 0 M NaCl to 1M NaCl in S30 buffer. Fractions containing proteins were pooled and concentrated using Centricon® centrifugal filters (3 kDa MW cut-off). The purity of the concentrated proteins was checked by sodium dodecyl sulphate-polyacrylamide gel electrophoresis and exact mass was determined by reverse phase liquid chromatography-mass spectrometry (LC-qTOF, Agilent, San Jose, USA).

Analysis of Nucleotides by HPLC—

Samples (30 μL) were acidified with 20 μL of 150 mM $H_2SO_4$ and mixed, followed by centrifugation at 20,800 g for 10 minutes at 4° C. Supernatant was collected and analyzed by HPLC using a hybrid anion exchange/reversed phase column (Vydac 3021C 4.6×250 mm, 10 μm, with the guard column of the same material). Mobile Phase A: 10 mM sodium phosphate (1:1 $Na_2HPO_4$:$NaH_2PO_4$) adjusted to pH 2.8 with glacial acetic acid. Mobile Phase B: 125 mM sodium phosphate (1:1 $Na_2HPO_4$:$NaH_2PO_4$) adjusted to pH 2.9 with glacial acetic acid. Separation was performed using following gradient, 0-2 min—0% B, 10 min—20% B, 22 min—100% B, 28 min—100% B. Flow rate was 2 ml/min and the UV absorbance was measured at 260 nm. Absolute concentration was determined using standard curves.

Results

Activation of Cell-Free Extracts for In-Vitro Protein Synthesis—

Figure 5:
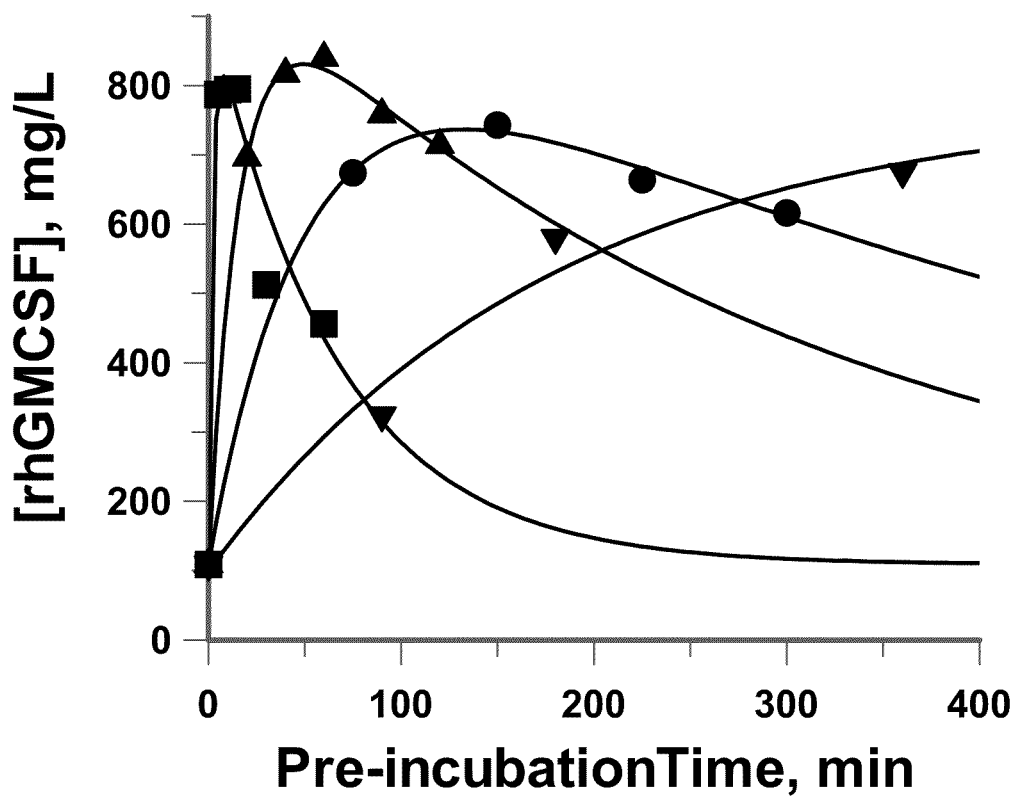
FIG. 5: Pre-incubation protein synthesis reaction profiles of extracts prepared from *E. coli* strain KGK10. Extracts were incubated at 42° C. (■), 37° C. (▲), 30° C. (●), and 25° C. (▼) for the indicated time, and aliquots were used for in-vitro synthesis of rhGM-CSF for 5 hrs, Protein synthesis yields were monitored by $^{14}$C leucine incorporation. Data were fit to $Y=A_{01}\exp(-k_1*t)+A_{02}\exp(-k_2*t)$ corresponding to a biphasic process.

Cell-free extracts were prepared from E. coli strain KGK10 (Zawada et al., supra). These extracts require pre-incubation prior to in-vitro protein synthesis. The yield of a model protein, rhGM-CSF producted at 5 hrs of cell-free reaction, was measured, where the reaction is linear with time (Zawada et al., supra), as a function of the time and temperature of the pre-incubation step, as shown in FIG. 5. The activation process is temperature dependent with full activation in as much as 10 min at 42° C. compared to 150 min at 30° C. Even though the rate of activation varies at different temperatures, the maximal yield is not significantly different. The activity decreases after full activation with highest decrease at 42° C., possibly due to non-specific protein precipitation or inactivation of critical factors, and is not the focus of this study. The available time window for harvesting fully activated extract during incubation is smaller at higher temperature. Moreover, a small change in the extract preparation method could change the profile significantly making it a hard to control process. This is particularly important for large-scale production. Therefore, the inventors typically activate their extracts at 30° C. for 150 min.

The pre-incubation process is thought to be required for the completion of run-off to free-up the ribosomes from endogenous message (Nirenberg 1963 supra) which in turn would lead to dissociation of polysomes into 70 S ribosomes and subunits. However, according to a recent report, the extract mainly contains 70S ribosomes and subunits with a relatively small amount of polysomes and the change in ribosome profile does not correlate with activity (Liu et al., supra). The authors of the same report also observed that the run-off reaction is complete within 20 min but full activation requires longer time suggesting that the freeing of ribosomes in not the only mechanism of activation. Moreover, background protein synthesis should occur if the run-off reaction is ongoing. The inventors did not detect background protein synthesis in their extract during the activation process.

Figure 6:
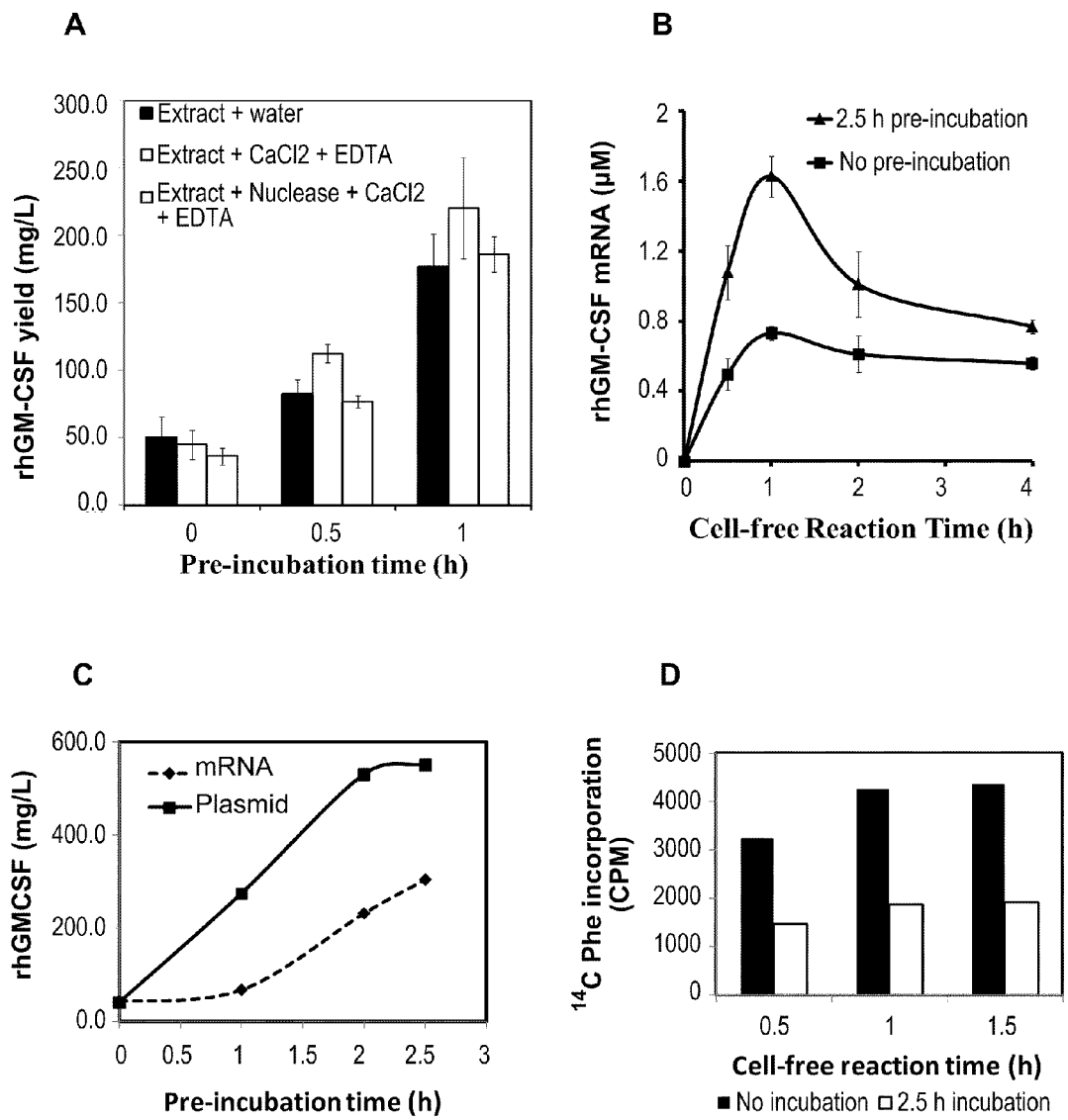
FIG. 6: Pre-incubation is not required for removal of endogenous message or activation of transcription. A) Comparison of pre-incubation profile/run-off reaction profile of extracts with and without nuclease treatment. Extracts were treated with *Staph. aureus* nuclease in the presence of CaCl$_2$ for removal of endogenous message followed by quenching of the nuclease activity by EDTA. The extract activity was monitored by $^{14}$C leucine incorporation into rhGMCSF. B) rhGMCSF mRNA levels during cell-free reactions of non-incubated and 2.5 incubated extracts. mRNA levels were monitored by $^3$H UTP incorporation. C) Comparison of pre-incubation profile with added mRNA Vs plasmid. D) PolyU directed $^{14}$C phenylalanine incorporation in non-incubated Vs 2.5 h pre-incubated extract.

Some researchers have tried nuclease treatment to remove endogenous message (Hofbauer et al., Eur J Biochem 122: 199-203; Ehrenfeld and Brown 1981. J Biol Chem 256: 2656-61). For the extract in this invention, however, removal of endogenous message by nuclease (Staphylococcus aureus) treatment did not change the activation profile relative to control (FIG. 6a). Thus, it appears that the pre-incubation process involves factors other than just the disassociation of polysomes by run-off of endogenous mRNAs.

One possible factor is the inactivation of transcription during extract preparation which requires heat to reactivate. If this were the case, the non-incubated extract would be unable to transcribe from a DNA template. To determine this, the inventors measured mRNA synthesis in incubated extract and non-incubated extract. Synthesis of mRNA was detected in non-incubated extract, though at a lower level than fully activated extract, suggesting that pre-incubation is not required for transcription per se (FIG. 6b). It appears that the transcription process is active. Moreover, when the cell-free protein synthesis reactions were carried out using purified mRNA of rhGM-CSF instead of plasmid, the non-incubated extract did not synthesize protein. Thus it is translation that requires pre-incubation for activation (FIG. 6c).

Following this, the inventors decided to probe the status of translation in the non-incubated extract. When polyuridylic acid (UUUn) was used, which lacks a start codon and can be translated by ribosomes without initiation, interestingly, non-incubated extract was able to synthesize polyphenylalanine (FIG. 6d). This suggests that the ribosomes are capable of elongation of new message and may not be engaged with the endogenous message. Also, the incubation process appears to negatively affect the elongation process as judged by decreasing yields. Translation of polyuridylic acid is not affected by the factors that affect initiation or if the translation is blocked at the initiation step (Clark 1980. Proc Natl Acad Sci USA 77: 1181-4; Agafonov et al., 2001. EMBO Rep 2: 399-402). Thus, these data suggest that the initiation step of protein synthesis is blocked and it is this particular step of translation that requires pre-incubation.

It has been hypothesized that the activation process probably involves activation or deactivation of certain factors that are involved in protein synthesis. For example, transcription regulator AraC has previously been reported to degrade during the run-off reaction (Zubay 1973. Annu Rev Genet. 7: 267-87). However, this hypothesis and in general, the process of activation has not been tested systematically.

With the advent of modern systems biology approaches to analysis of biological samples and processes, the inventors have undertaken a global analytical approach to understand the complex nature of in vitro transcription and translation. In this report, a unique proteomic profiling approach was used to investigate the changes that occur during the run-off reaction. Global metabolite profiling was also conducted.

Proteomic Analysis of Pre-Incubation Process—

Figure 7A:
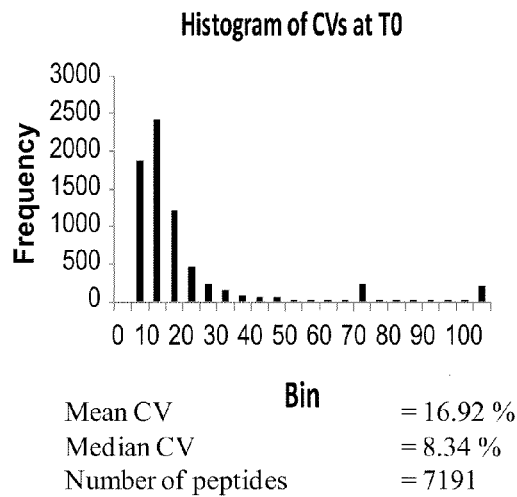
FIG. 7: Label-free proteomic profiling of pre-incubation process. A) Reproducibility of label-free proteomic profiling method for 7191 peptides. B) Pie-chart showing the functional categories of proteins profiled. C) Intensity Vs time profiles of peptides detected by LC/MS during pre-incubation process. Profiling was carried out on samples collected at 0, 2.5 and 5 h at 30° C. corresponding to the initial, maximal, and late pre-incubation process. The gray-shaded lines show intensities of all the peptides profiled during pre-incubation with darker gray indicating higher intensity. Selected peptides showing decrease in intensity over the pre-incubation time are highlighted in black color for illustration purpose. D) Intensity Vs time plots of selected peptides belonging to cold shock proteins CspC, CspE and H-NS during the pre-incubation at 30° C. Average intensities of 2 peptides from each protein are plotted with error bars indicating standard deviation over three independent extract pre-incubation reactions. n=3.

Proteomics can be used to characterize a very complex system and obtain information about the composition and dynamics of the proteome. There are several methods for doing proteomic analysis and selecting the one that best suits the problem at hand is important. The inventors have developed a unique approach of performing label-free proteomic profiling, which involves generation of an in-depth peptide library containing accurate mass and retention time data obtained from MS/MS analysis. The experimental samples are then analyzed in MS mode and searched against the generated library, thereby, yielding a reliable intensity value for almost all of the peptides queried in every sample run on LC-MS. This relative quantification method offers reliable detection of changes in the levels of more than 1500 proteins represented by ~7200 unique peptides with median coefficient of variation (CV) of 8.4%, the smallest CV ever reported in a proteome-wide study (FIG. 7a).

Figure 7B:
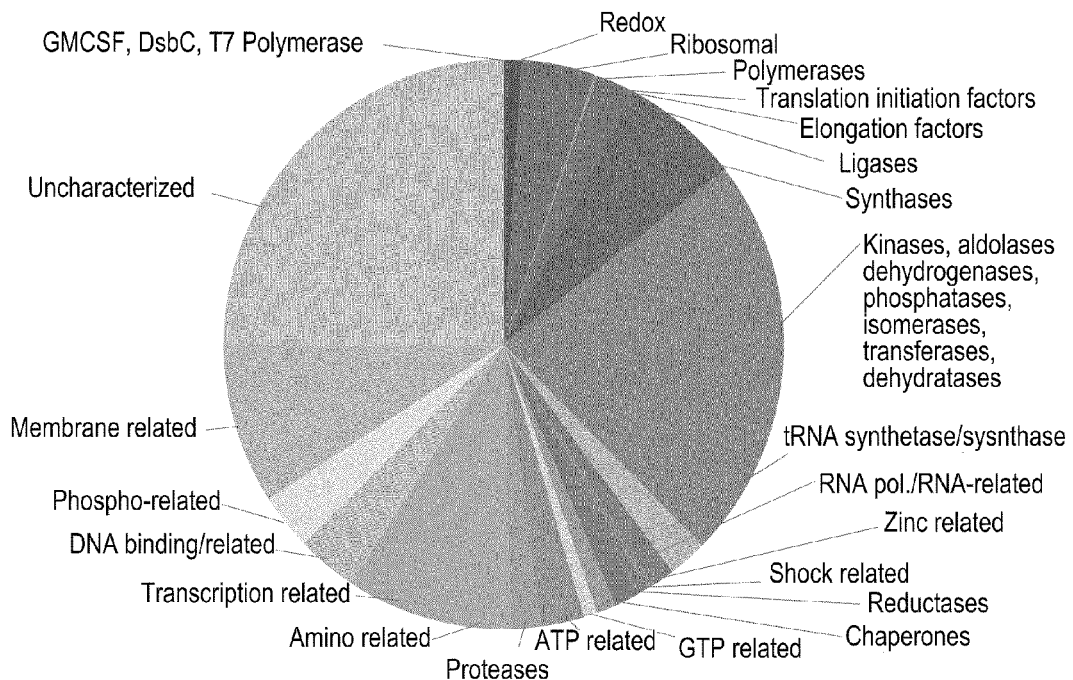

The different functional categories of proteins detected are shown in FIG. 7b. Using this method, the extract proteome was profiled during pre-incubation process at 0, 2.5 and 5 h at 30° C. corresponding to the initial, maximal, and late pre-incubation process shown in FIG. 5. An ANOVA analysis was conducted to see the consistent trends in 3 independent extracts. Among all the profiled proteins, only cold shock protein E (CspE), cold shock protein C (CspC), DNA binding protein H-NS(H-NS), adenylate kinase, ATP synthase, outer membrane protein A (ompA), and cell division protein FtsZ were found to decrease significantly and consistently (FIGS. 7c and 7d). Cold shock proteins CspE and H-NS showed strongest decline at 2.5 h, which corresponds to the full activation time. Interestingly, proteins CspE, CspC and H-NS all belong to cold shock family of proteins, which are known to interact and inhibit cellular transcription and translation machinery (Hofweber et al., 2005 FEBS J272: 4691-702), thus for the first time pointing to this phenomenon as an important player in extract activation process.

Figure 8:
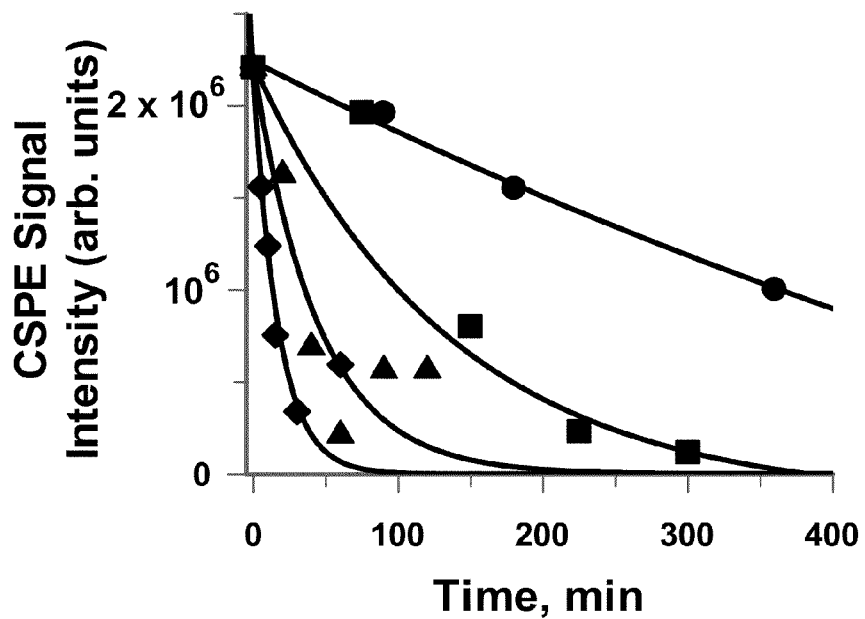
FIG. 8: (A) Kinetics of CspE decay at 25 (●), 30 (■), 37 (▲), and 42 (♦)° C., monitored by LC-MS during the pre-incubation reaction. Data were fit to a single exponential decay $Y=A_0\exp(-k_{decay}*t)$. (B) Relationship between the first-order rate constant for CSP decay and the corresponding first-order rate constants for extract activation, from FIG. 1, measured at several temperatures. The data were fit to a linear free energy relationship $k_{decay}=Ck_{activation}^\beta$, where β=0.64±0.06 for CSPC, β=0.75±0.14 for CspE, and β=0.81±0.05 for HNS, measures the sensitivity of CSP decay kinetics as a function of the rate of extract activation.
Figure 8:
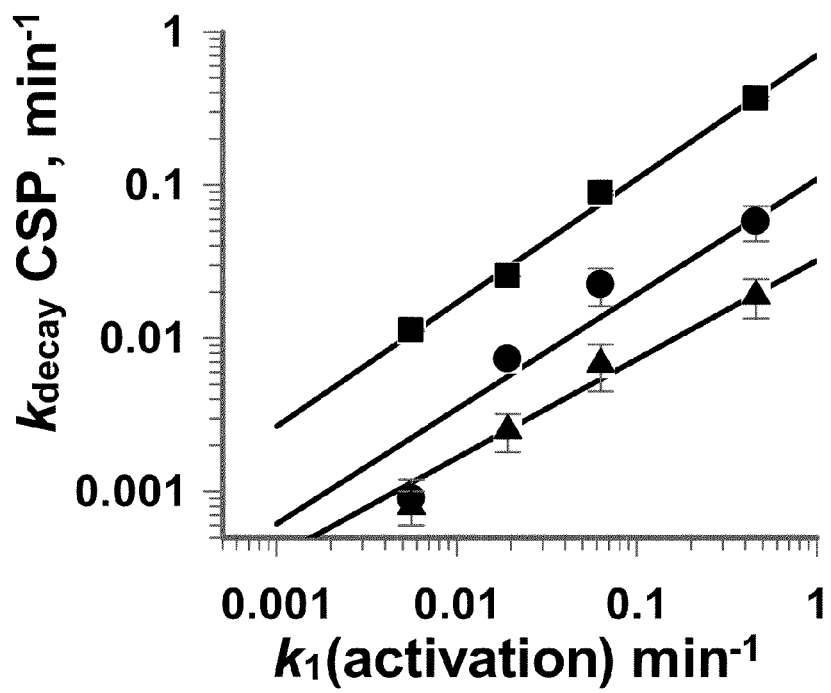

The decrease in the levels of cold shock proteins could be correlated with the activation profiles at different temperatures (FIG. 8). For H-NS, peptides close to C-terminus decreased while other peptides remained stable during the incubation. H-NS is a known substrate of OmpT protease with a cleavage site (K87-R90) near the C-terminus. The fact that the extract of this invention contains this protease and that the inventors observed clipping of exogenous H-NS at the OmpT cleavage site suggests that H-NS is subjected to proteolysis during pre-incubation. Similarly, the protein sequences of adenylate kinase (ADK) and ATP synthase have OmpT protease sites (KR, RR, RK, RA, KA) and the decrease in the levels of these proteins shown in FIG. 7c could also be due to OmpT proteolysis. However, the protein sequences of CspE and CspC do not have OmpT cleavage sites.

An alternative mechanism for loss of CSPs lacking OmpT cleavage sites during the pre-incubation could be due to precipitation as has been observed previously (Liu et al., supra). It was suggested that the removal of protein synthesis inhibitory factors by precipitation could possibly be one of the mechanisms of extract activation. During the pre-incubation process, precipitation of some material was observed and the amount of precipitate increased with time. The precipitate was collected by centrifugation and subjected to proteomic analysis. The CSPs were found to be present in the precipitate and the amount present in precipitate increased with the pre-incubation time. It is unclear as to why these proteins precipitate when present in extract as precipitation of purified proteins in solution is not observed. It is hypothesized that CSPs co-precipitate with RNA/DNA and/or membrane vesicles during incubation.

These data drew the inventors' attention to established extract production processes and the possibility of cold shock induction during cell harvesting. For the extracts analyzed by proteomics, the cell harvesting process involved recirculation of cells through the heat exchanger for over an hour until the temperature reached below 10° C. The cells were then centrifuged in a pre-cooled (4° C.) centrifuge and washed with ice cold S30 buffer followed by homogenization. Extracts produced using this process showed variable pre-incubation profiles and at times gave low yields. The entire process which takes several hours could elicit cold stress response resulting in variable induction of transcription/translation inhibitory CSPs.

Figure 9:
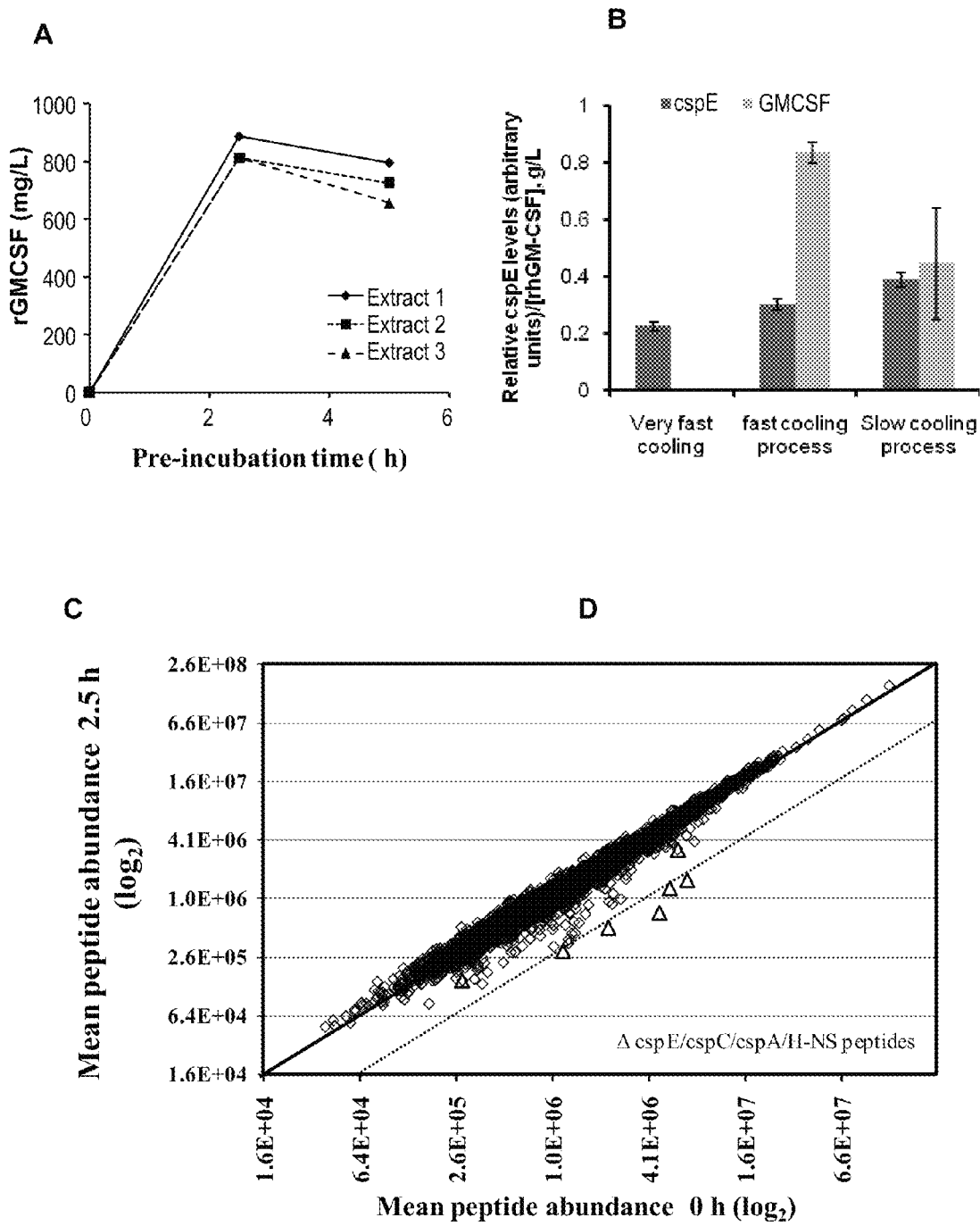
FIG. 9: Faster cooling process during cell harvesting produces highly active extracts with predictable pre-incubation behavior. A) Pre-incubation profiles of extracts from 3 independent fermentor runs harvested with the fast cooling process. B) Comparison of CSP levels (CspE) and protein synthesis yield (rhGM-CSF) in extracts prepared from quenched, slow cooled and fast cooled cells. The CspE levels are normalized to endogenous GAPDH. * indicates p-value <0.001, compared to slow cooling process. Protein synthesis data was obtained for quenched cells. C) Proteomic profiling of pre-incubation process of extract prepared with fast cooling process. Peptides belonging to cold shock proteins CspE, CspA, CspC and H-NS are indicated with Δ symbol.

In order to investigate the role of cold stress during harvesting on the extract activity, the cells were rapidly harvested and cooled down to 4° C. (within 10 min) also using a heat exchanger but without slow recirculation. The extracts produced using the fast cooling process showed highly consistent pre-incubation profiles (FIG. 9a). Interestingly, the extract activity showed an inverse relationship to CSP levels (FIG. 9b) with the extract prepared from fast cooled cells showing significantly lower CSP levels (p-value <0.001) and high protein synthesis activity compared to the extract prepared from slow cooled cells. The CSP levels in the extract prepared from fast cooled cells were higher than extract prepared from the quenched cells (5 ml broth quenched in 20 ml of methanol:water, 80:20 v/v, pre-cooled to −80° C.), suggesting that even fast cooled cells experience some cold stress. Unfortunately, due to the volume limitations (minimum 30 ml) of the industrial scale homogenizer, extract from the quenched cells (5 ml volume) could not be prepared.

Comparison of global proteomic analysis of non-incubated and 2.5 h incubated extract prepared with the fast cooling process is shown in FIG. 9c. Again the cold shock proteins CspE/C and H-NS were found to decrease the most. In these extracts, CspA, a transiently induced major cold inducible protein, seems to be absent or possibly below the detection limits as evidenced by the absence of the unique peptides from this protein that had previously been detected in extracts prepared by slow cooling.

Inhibition of Cell-Free Protein Synthesis by Purified Cold Shock Proteins—

Figure 10:
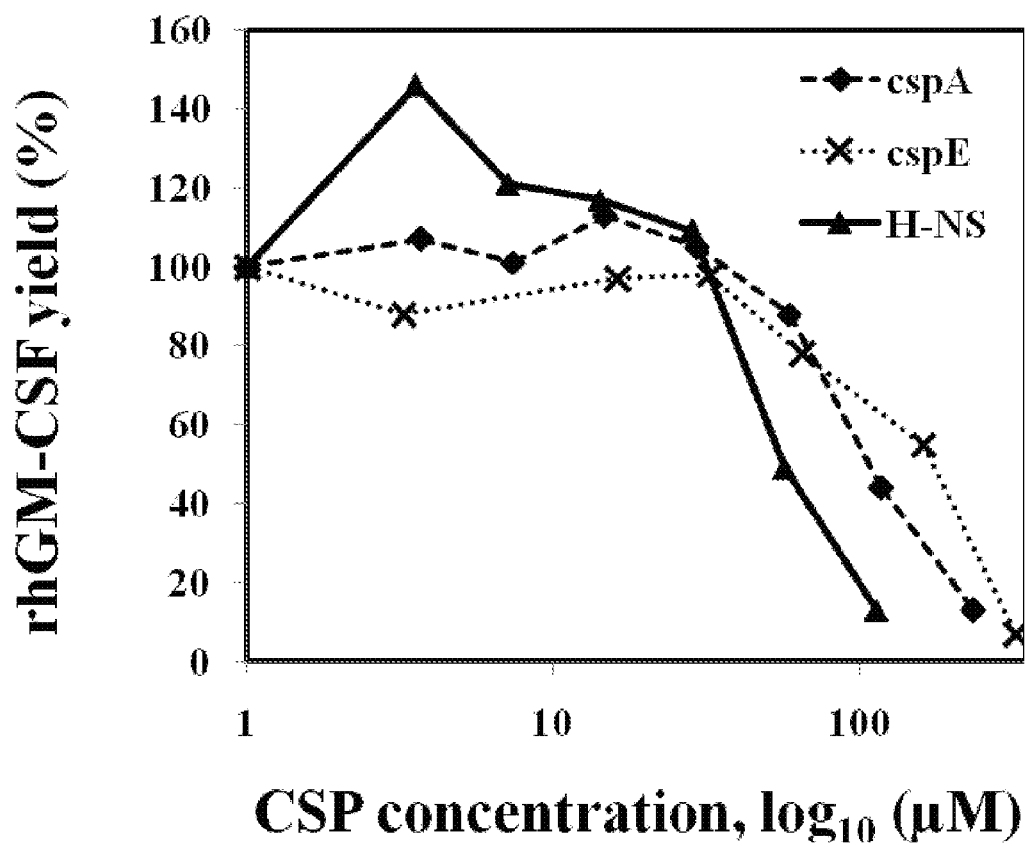
FIG. 10: Effect of purified CspA, CspE and H-NS on in-vitro synthesis of rhGM-CSF. Purified proteins were added at the beginning of the cell-free reactions and the rhGM-CSF synthesis was monitored after 5 h by $^{14}$C leucine incorporation as described by Zawada et al. (*Biotechnol. Bioeng.* 2011, 108(7), 1570-78).

Purified CSPs have been previously shown to inhibit in-vitro coupled transcription-translation of cold shock and non-cold shock proteins (Hofweber et al., 2005. FEBS J272: 4691-702; Bae et al., 1999. Mol Microbiol 31: 1429-41). In order to confirm that the CSPs exhibit similar activity in the extracts of this invention, rhGM-CSF synthesis was performed in the presence of various concentrations of purified CSPs (FIG. 10). At lower concentrations, H-NS and CspA showed increased protein synthesis with H-NS showing as much as 45% stimulation at 3.6 µM level.

At higher concentrations, inhibition of protein synthesis was observed for all the proteins studied. At 114 µM concentration, 87%, inhibition was observed for H-NS while CspA and CspE showed 87% and 93% inhibition at 237 µM and 324 µM concentration. H-NS showed the strongest biphasic response of stimulation and inhibition. For CspA, the results of this study are in line with a previous report (Hofweber et al., supra), which showed 50% inhibition of chloramphenicol acetyltransferase expression in E. coli cell-free system by T. maritime CspA at 140 µM concentration. For CspE, 50% inhibition of rGM-CSF expression was observed at approximately 160 µM concentration, which is higher than earlier report of 37% and 72% inhibition of CspA expression at 12 and 24 µM concentration, respectively. The difference in the inhibition concentration could be product dependent, with inhibition of CSP expression by other CSPs being the strongest as csps are known to repress the expression of other csps in cells (Bae et al., supra). While the concentration of CspE and H-NS in the cold-shocked E. coli cells in not known, CspA has been estimated to be present at approximately 100 µM concentration during cold shock (Jiang et al., 1997. J Biol Chem 272: 196-202). Hence, the concentrations that showed in-vitro inhibition of protein synthesis in this study are in the physiological range.

Deletion of Cold Shock Proteins CspE, CspC, CspA and H-NS—

Figure 11:
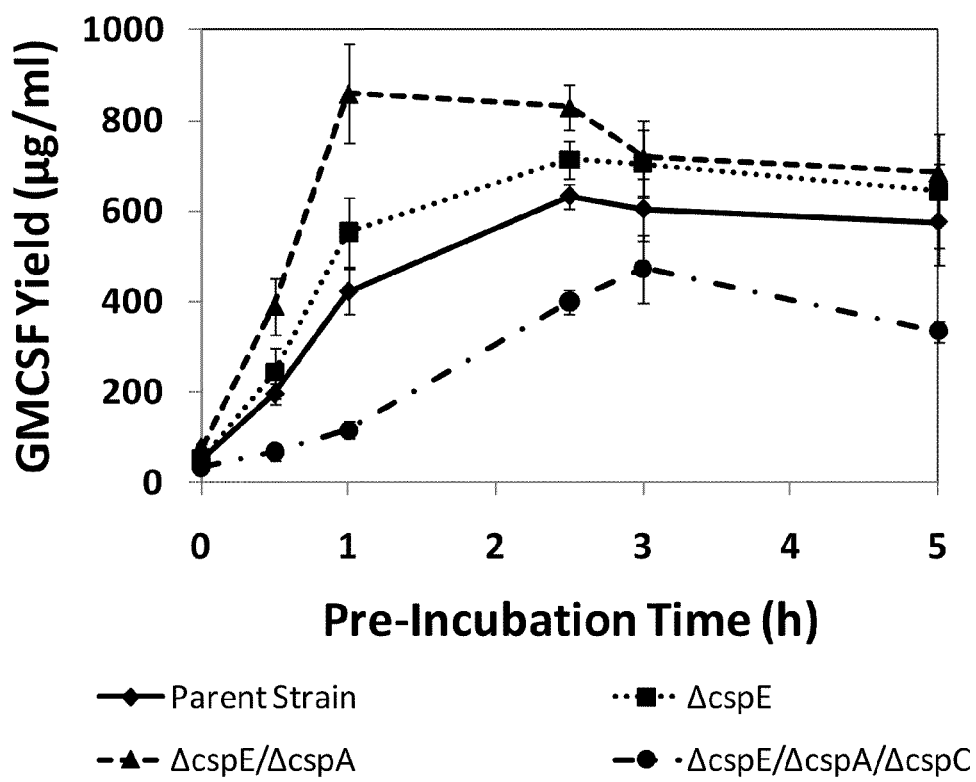
FIG. 11: Effect of deletion of cold shock proteins on pre-incubation profile of *E. coli* cell-free extract. Extracts prepared from cold shock deletion mutants ΔcspE, ΔcspE+ΔcspA, ΔcspE+ΔcspA+ΔcspC and parent strain were pre-incubated. 30° C. for the indicated time, and aliquots were used for in-vitro synthesis of rhGM-CSF for 5 hrs. Protein synthesis yields were monitored by $^{14}$C leucine incorporation as described by Zawada et al., supra.

Single, double and triple deletion mutant strains were created by deleting CspE (ΔcspE), both CspE and CspA (ΔcspE+ΔcspA), the three proteins CspE, CspA and CspC (ΔcspE+ΔcspA+ΔcspC) and another combination of three proteins, CspE, CspA and H-NS (ΔcspE+ΔcspA+Δhns). Pre-incubation profiles of extracts prepared from these mutants, except for ΔcspE+ΔcspA+Δhns strain which showed no activity, are shown in FIG. 11. Parent strain extract was fully activated by 2.5 h which is typical for these extracts. However, mutants exhibited changes in the activation profile with mutants ΔcspE and ΔcspE+ΔcspA yielding higher activity while mutants ΔcspE+ΔcspA+ΔcspC and ΔcspE+ΔcspA+Δhns performing poorly. Interestingly, ΔcspE+ΔcspA mutant was fully activated by 1 h with almost double the activity compared to the parent strain. This confirms the hypothesis that the CSPs are inhibitory and their removal leads to decreased inhibition and faster activation. This is the first report of a significant and reproducible change in the extract activation profile caused by deletion of a protein, a possible inhibitory factor.

Pre-Incubation is not Required for Activation of Nucleotide Triphosphate Synthesis—

Energy required for cell-free protein synthesis can be supplied using nucleotide monophosphates owing to their fast and efficient conversion into nucleotide triphosphates (Calhoun and Swartz, supra). Since nucleotide monophosphates were used as the energy source in the system of this study, nucleotide analysis was performed to see if non-incubated extracts are incapable of synthesizing nucleotide triphosphates and if incubation is required to activate their synthesis. During the cell-free reaction of both non-incubated and incubated extract, ATP and other nucleotides are rapidly generated from the supplied nucleotide monophosphates. This suggests that the pre-incubation process is not required for the activation of synthesis of ATP and other nucleotides required for transcription and translation. Deletion of CSPs did not cause any change in the time-concentration profiles of these nucleotides. Therefore, earlier activation of Δ cspEA extract cannot be correlated to faster energy generation.

Discussion

In this report, the present inventors applied a systems approach, differential proteomic profiling, to discover cold shock proteins as primary inhibitors of in-vitro protein synthesis in E. coli. Considering the complexity of the transcription and translation process, and the absence of hypothesis, a global approach was appropriate. The unique label-free proteomic profiling method developed utilized an accurate mass and retention time database of more than 7,000 peptides representing over 1500 proteins built by untargeted MS/MS. The list of identified peptides was then queried in the raw MS data for ion intensities. The analysis was still "untargeted" in nature, as the peptide library was built in an unbiased fashion. This analysis allowed for proteome-wide differential profiling with raw ion intensities, giving more representative ion statistics as opposed to methods such as spectral counting. At the same time, it obviated the need for special software for label-free quantification. Overall, this method offers a highly robust and simple path for all laboratories with mass spectrometry capabilities with limited software resources to conduct differential proteome profiling of hundreds to thousands of proteins.

The finding of the involvement of cold shock proteins in extract activation using such a systems approach is significant in that it challenges a well-accepted but inadequately supported hypothesis that the inactivity of prepared E. coli extracts is due to engagement of ribosomes with endogenous message. It also corroborates the power of a systems approach when no reliable hypothesis exists or the hypothesis that exists seems untenable. The important impact of chilling proved to be one of the critical factors in the successful development of a robust process for commercial scale in-vitro synthesis of a wide spectrum of proteins/peptides which are difficult/impossible to synthesize using cell-based methods. This study serves as a unique application of systems biology analysis for industrial-scale process development.

In-vitro protein synthesis was demonstrated in early 1960's (Nirenberg 1963, supra). Since then, the technique, particularly for the E. coli system, has evolved tremendously as a biochemical tool as well as an alternative to conventional cell-based techniques for commercial protein production. E. coli cell-free extract preparation involves fermentation, cell harvesting, lysis and clarification. The cell collection and downstream processing steps are typically carried out at lower temperature (~10° C.) to preserve cellular machinery and ribosomes. Interestingly, the extract produced is unable to synthesize proteins and warming is required. It has been proposed that the ribosomes are engaged with the endogenous message and that they need to be dissociated from it for accepting exogenous message. However, the possible effect of cold stress, which is well-known to block protein synthesis, on extract activity has been completely ignored in the context of extract production.

The present inventors provide experimental evidence that the cold shock proteins are induced during this process and pre-incubation activates protein synthesis. Their study is the first to shows that the cold shock proteins are selectively removed, possibly by precipitation/proteolysis, during this warming up step and their removal correlates with the activation of protein synthesis.

It is well established that cold shock proteins are induced when E. coli cells are subjected to a temperature of 15° C. or below which is commonly referred to as "cold shock" (Phadtare 2004. Curr Issues Mol Biol 6: 125-36). During the cold stress, the expression of these proteins inversely correlates with the global protein synthesis rate (Horn et al., 2007. Cell Mol Life Sci 64: 1457-70). Synthesis of non-cold shock proteins is almost completely blocked during the peak induction of CSPs and protein synthesis resumes when the CSPs drop to near pre-cold shock levels. This is not surprising considering that these proteins are known to inhibit both transcription and translation processes (Hofweber, supra). The CSPs appear to be induced due to the cold stress they are inadvertently subjected to during cell harvesting and extract preparation processes, causing the inhibition of in-vitro protein synthesis.

One way to reduce the cold stress and induction of CSPs would be to harvest the cells as fast as possible. In our hands, faster harvesting at even lower temperatures in 15-20 min led to improved extract activity, with no change in activation profile. However, even with a fast harvesting, CSPs are still induced, albeit to a lower level and are still removed during the pre-incubation. The deletion of genes encoding several CSPs was attempted to decrease the need for activation and not surprisingly, resulted in both faster activation and significantly higher protein synthesis activity compared to the extract made with the wild-type strain.

The findings presented here on cold shock proteins as primary inhibitors of in-vitro protein synthesis are supported by published reports. At cold temperatures, translation initiation is known to be blocked while the elongation of already initiated protein continues for 25 min, followed by accumulation of 70S monosomes and subunits (Friedman et al., 1971. J Mol Biol 61: 105-21; Broeze et al., 1978. J Bacteriol 134: 861-74). Therefore, in the absence of new protein synthesis, the elongation of already initiated message should be completed during the extract preparation process, which takes more than 2 hrs. This in turn should result in dissociation of polysomes. Indeed, the prepared extract does contain free ribosomes (Liu et al., supra). This is further supported by the fact that our non-incubated extract can synthesize polyphenylalanine. Moreover, no background protein synthesis was detected using non-incubated extract and even after nuclease treatment, which should remove endogenous message, the extract could not be activated.

It was concluded that the endogenous message is not an interfering factor that needs to be removed by pre-incubation. It was proposed then that the term "run-off" reaction be replaced by "pre-incubation" or "activation step" when describing cell-free protein synthesis extract activation.

The fact that the non-preincubated extract is able to synthesize mRNA and is also able to elongate polyphenylalanine suggests that the initiation step of translation is blocked, which interestingly is proposed to be involved in translation inhibition by cold shock proteins.

In summary, CSPs are induced during harvesting and extract preparation processes carried out at cold temperatures and they block in-vitro coupled transcription/translation. These inhibitory factors are removed during the so called "run-off reaction" and their removal not only corresponds to the activation of translation, but is directly responsible for activating the extract.

All patents, patent applications, and other publications, including GenBank Accession Numbers, cited in this application are incorporated by reference in the entirety for all purposes.

What is claimed is:

1. A method for enhancing recombinant protein production in a cell-free protein synthesis system comprising:
   contacting a cell lysate prepared from prokaryotic cells comprising a recombinant genomic modification that abolishes CspE expression, and an exogenous nucleic acid template encoding a protein; and
   producing the protein encoded by the exogenous nucleic acid template in the cell-lysate.

2. The method of claim 1, wherein the recombinant genomic modification comprises at least one nucleotide substitution or deletion in the genomic sequence encoding for the CspE.

3. The method of claim 1, wherein the prokaryotic cells further comprise a recombinant genomic modification that abolishes CspA expression.

4. The method of claim 3, wherein the recombinant genomic modification comprises at least one nucleotide substitution or deletion in the genomic sequence encoding for the CspA gene.

* * * * *